United States Patent
Karandikar et al.

(10) Patent No.: US 6,207,464 B1
(45) Date of Patent: *Mar. 27, 2001

(54) RIGIDIZED MONOMETHINE CYANINES

(75) Inventors: Bhalchandra M. Karandikar, Tigard, OR (US); Alan S. Waggoner, Pittsburgh; Ratnakar B. Mujumdar, Glenshaw, both of PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/143,070

(22) Filed: Aug. 28, 1998

Related U.S. Application Data

(62) Division of application No. 08/474,056, filed on Jun. 7, 1995, now Pat. No. 5,852,191.

(51) Int. Cl.$^7$ ..................... G01N 33/533; G01N 33/545; G01N 33/552; C12N 9/96
(52) U.S. Cl. ................. 436/546; 435/6; 435/7.2; 435/188; 436/519; 436/527; 436/530; 436/531; 436/800; 530/391.3; 530/402
(58) Field of Search ................. 530/391.3, 402; 435/188, 6, 7.2; 436/519, 530, 527, 546, 800, 531

(56) References Cited

U.S. PATENT DOCUMENTS

| | | | |
|---|---|---|---|
| 2,432,080 | 12/1947 | Anish | 260/240 |
| 2,541,400 | 2/1951 | Brooker et al. | 260/240.7 |
| 3,148,187 | 9/1964 | Heseltine | 260/240.4 |
| 3,250,780 | 5/1966 | Rai et al. | 260/307 |
| 3,729,467 | 4/1973 | Zweldler et al. | 260/240.7 |
| 4,064,136 | 12/1977 | Lowe et al. | 260/304 |
| 4,337,063 | 6/1982 | Mihara et al. | 23/230 B |
| 4,404,289 | 9/1983 | Masuda et al. | 436/538 |
| 4,405,711 | 9/1983 | Masuda et al. | 435/4 |
| 4,774,339 | 9/1988 | Haugland et al. | 548/405 |
| 4,916,711 | 4/1990 | Bayer et al. | 372/83 |
| 5,187,288 | 2/1993 | Haugland et al. | |
| 5,248,782 | 9/1993 | Haugland et al. | 548/110 |
| 5,268,486 | 12/1993 | Waggoner et al. | 548/427 |
| 5,274,113 | 12/1993 | Kang et al. | 548/405 |

FOREIGN PATENT DOCUMENTS

| | | |
|---|---|---|
| 610064 | 10/1948 | (GB) . |
| 618889 | 3/1949 | (GB) . |
| 1529202 | 10/1978 | (GB) . |
| PCT/US92/08350 | 5/1993 | (WO) . |

OTHER PUBLICATIONS van Koeveringe et al., Novel pyrromethenes 1–Oxygen and 1–sulfur analogues; evidence for photochemical Z–E isomerization, Recl. Trav. Chim. Pas–Bas, vol. 96, p. 55 (1977).

Lapworth et al., Oxidation Products of Oleic Acid. Part I. Conversion of Oleic Acid into Dihydroxystearic Acid and the Determination of the Higher Saturated Acids in Mixed Acids from Natural Sources, J. Chem. Soc., 1628 (1925).

Saito, et al., Combination of Borane–Dimethyl Sulfide Complex With Catalytic Sodium Tetrahydroborate as a Selective Reducing Agent For a–Hydroxy Esters, Versatile Chiral Building Block from (s)–(–) Malic Acid, Chem. Letters, 1389–1392 (1984).

Newkome, et al., Nitrile–Stabilized Carbanions. Nucleophilic Substitution Reactions on Bromopyridines, J. Org. Chem., 1988, 53, 786–780.

Saito, et al., Synthetic Studies Using a β–Unsaturated Nitriles: A Convenient Preparation of 1,3–Bezothiazole Derivatives, Synthesis, (3), p. 210–11 (1983).

McElvain, et al., Orthoesters and Related Compounds from Malono–and Succinonitriles, JACS, vol. 71, p. 40–46 (1949).

Ramos, et al., Tautomerism of Bis(2–Benzothiazolyl)Arylmethanes, Heterocycles, vol. 29, No. 1, p. 165–180 (1989).

Avendano et al., Tautomerism of bis(2–benzothiazolyl)methanes, Can. J. Chem., vol. 67, p. 1467–1473 (1988).

Vos de Wael, et al., Pyrromethene–BF$_2$ complexes (4,4'–difluoro–4–bora–3a,4a–diaza–s–indacenes). Synthesis and luminescence properties, Recl. Trav. Chim. Pay–Bas, vol. 96, p. 306 (1977).

(List continued on next page.)

Primary Examiner—Mary E. Ceperley
(74) Attorney, Agent, or Firm—Kirkpatrick & Lockhart LLP

(57) ABSTRACT

Boron complexes of certain bis-heterocyclic compounds are provided. The complexes resemble monomethine cyanines and are useful for imparting fluorescent properties to materials by covalent and noncovalent association. The compounds have the following general formula:

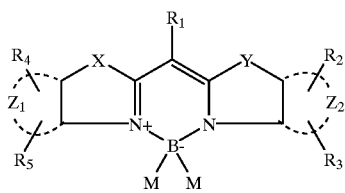

wherein the dotted lines $Z_1$ and $Z_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur, and $R_1$ through $R_5$ represent various atoms or groups and M is Cl or F.

26 Claims, 3 Drawing Sheets

OTHER PUBLICATIONS

Wories, et al., A novel water–soluble fluorescent probe: Synthesis, luminescence and biological properties of the sodium salt of the 4–sulfonato–3,3',5,5'–tetramethyl–2,2'–pyrromethen–1,1'$BF_2$ complex, Recl. Trav. Chim. Pays–Bas 104, 288–291 (1985).

Treibs, et al., Difluorboryl–Komplexe von Di– und Tripyrrylmethen, Liebigs Ann. Chem., vol. 718, p. 208–223 (1968).

Bodipy: The New Fluorescein Substitute, Bioprobes, No. 10, (Molecular Probes, Inc., Eugene, Or.) (Dec. 1989).

Haugland, *Handbook of Fluorescent Probes and Research Chemicals*, ($5^{th}$ ed. 1992) Molecular Probes, Inc., Eugene, OR, pp. 9–110, 159–180, 203–274.

*Reactive Bodipy Dyes,* (Molecular Probes, Inc., Eugene, OR 1992), pp. 1–3.

Shah et al., Pyrromethene–$BF_2$ Complexes as Laser Dyes:1., *Heteroatom Chemistry* (vol. 1, No. 5, 1990).

Kaplan et al., "Synthesis and Luminescence—Spectral Characteristics of the Chelates of Boron with Diheterylamines" (1991) translated from *Zhurnal Organicheskai Khimii,* vol. 27, No. 4, pp. 872–877, Apr. 1991.

Kang and Haugland, "Spectral Properties of 4–Sulfornato–3, 3',5'5'—Tetramethyl–22'–Pyrromethen–1,1'—Barandifluoride Complex (Bodipy), Its Sodium Salt, and Protein Derivatives," SPIE, vol. 1063 *New Technologies in Cytometry* (1989), pp. 68–73.

Douglass et al., "Diazobarayclic Cations. III. A Homomorph of 9, 10–Dihydroanthracene (1)," *Journal of Heterocyclic Chemistry* (vol. 10, 1973), pp. 255–257.

Scheibe and Daltrozzo, *Advances in Heterocyclic Chemistry,* vol. 6, p. 153–81 (Academic Press 1965).

Ramos et al., "Crystal and Molecular Structure of 6–Phenyl–13H–Pyrimido [4,3–b:6,1–b] bis–benzothiazoluim–12 triiodide," *J. of Crystallographic and Spectroscopic Research,* vol. 21, No. 2, 1991, pp. 179–182.

Abbotto, "Novel Heteroaromatic and Heteroalicyclic Metal Methanates, $ML_2$ {L=Bis(2–Benzothiazolyl) and Bis [2–($_2$–Thiazolinyl)]}", Gazzettia Chimica Italiana, 121, 1991, pp. 303–305.

Hugel, A Facile Synthesis of (+)2–(4–Chlorophenyl)–a–Methyl–5–Benzoxazoleacetic Acid (Benoxaprofen) Comm. 15, pp. 1075–1080 (1985).

Muller et al., 21.$C_2$–Symmetric 4,4',5,5'–Tetrahydrobi(oxazoles) and 4,4',5,5'–Tetrahydro–2,2–'methylenebis[oxazoles] as Chiral Ligands for Enentioselective Catalysis, Hel. Chim. Acta, 74, 232–240 (1991).

Hamer, *The Cyanine Dyes and Related Compounds* (John Wiley & Sons, New York 1964), pp. 32–85.

Ramos, et al., "Reactivity of Aryl–and Heteroarylmalonates against ortho–Dinicleophiles. Triaryl (heteroaryl) methane Synthesis", *J. Hetero. Chem.* 24, 247 (1987).

D. M. Sturmer and W. S. Gaugh, "Spectral Sensitization by Sterically Hindered Chromophores", Photographic Science and Engineering, vol. 19, No. 5 (Sep.–Oct. 1975), pp. 273–278.

T. Ramos et al., "Crystal and molecular structure of 6–phenyl–13H–pyrimido [4,3–6: 6, 1–b] bis–benzothiazolium–12 trliodide," J. Crystallographic and Spectroscopic Research, vol. 21, No. 2 (Apr. 1991), pp. 179–182.

G. Scheibe et al., "Das Franck–condon–Prinzip und die Lichtabsorpotion von Merocyaninen", Z. physik, Chem. Neue Folge, Bd. 64, S. 97–114 (1969).

RIGIDIZED MONOMETHINE CYANINES

The present application is a Division of U.S. patent application Ser. No. 08/474,056 filed Jun. 7, 1995, which issued as U.S. Pat. No. 5,852,191 on Dec. 22, 1998.

This invention was made with Government support under Contract NSF-DIR-8920118 awarded by the Public Health Service of the United States Department of Health and Human Services.

BACKGROUND OF THE INVENTION

1. Field of the Invention

The present invention relates to chemical dyes which can be used as fluorescent markers, and more particularly relates to monomethine cyanine-based compounds which have been sterically rigidized by the inclusion of a bridging boron atom between the compound's heterocyclic groups and which may be produced or chemically modified to include reactive or other groups to allow the compounds to covalently or noncovalently associate with a material to thereby impart fluorescent properties to the material.

2. Description of the Invention Background

Fluorescent dyes are generally known for imparting fluorescence to biological and nonbiological materials and have been used to detect various biological or other materials by procedures such as fluorescence microscopy, fluorescence immunoassay techniques, and flow cytometry. The primary advantages of fluorescent dyes compared with dyes detectable only through light absorption include (i) the emission of light by fluorescent dyes at a wavelength different from their excitation wavelength; (ii) the greatly enhanced detectability of fluorescence emission compared to light absorption; and (iii) the generally minimal level of background fluorescence in most biological materials.

A common method for labeling biological and nonbiological materials with fluorescent dyes is to create a fluorescent complex through covalent bonding between groups on the dye molecules and compatible groups on the material. In this way, material such as, for example, cells tissues, amino acids, proteins, antibodies, enzymes, drugs, hormones, nucleotides, nucleic acids, polysaccharide, and lipids may be chemically labeled and quantified or may be used as fluorescent probes that bind specifically to target materials (genetic sequences, haptens, antibodies, analytes, etc.) that are to be detected by fluorescence methods. Polymer particles, cells, and other materials labeled with fluorescent dyes can also be used as fluorescent standards in flow cytometers, imaging microscopes, and other fluorescence-based detection equipment. Minute fluorescent polymer particles can also be used as labels in immunofluorescence tests, toxicology testing, and analysis of genetic sequences. Because of their utility in research and medicine, a large market has developed for fluorescent reagents including prepared protein, antibody, and nucleic acid, and other probes pre-labeled with detectable fluorescent or fluorescent dye compounds.

Because most dye molecules are either nonfluorescent or only weakly fluorescent, available fluorescent dye markers have been derived from a relatively limited number of fluorescent aromatic structures. New fluorophores with optimal properties are rarely developed. Two common classes of fluorescent dyes are those derived from the fluorescein and rhodamine chromophores. Fluoresceins fluoresce green light whereas rhodamines fluoresce in the green-orange and red regions of the spectrum. The rhodamines are difficult labeling reagents to use, are not particularly fluorescent when bound to proteins, and often cause the precipitation of the labeled protein when the dye-to-protein ratio is greater than 2:1. One particular fluorescein dye, fluorescein isothiocyanate ("FITC"), and its conjugates, enjoy wide acceptance primarily because they have a relatively high extinction coefficient and have a high quantum yield. (Quantum yield is generally related to a molecule's rigidity or planarity and indicates the molecule's propensity to fluoresce, i.e., give off energy as light, rather than give off heat when energy is provided to the molecule.) However, fluorescein dyes have a number of disadvantages, including their strong tendency to photobleach when illuminated by a strong excitation source such as the lamps used in fluorescence microscopes. When a fluorescent compound photobleaches, a large percentage of the compound's fluorescence may be lost within seconds of illumination, resulting in a rapidly diminishing image. Also, when performing fluorescence assays, the loss of image through time by photobleaching makes quantifying results much more difficult and will ultimately result in a decreased ability to detect the analyte. Reagents, such as propyl gallate and p-phenylene-diamine, may retard but do not entirely eliminate photobleaching. The fluoresceins also have a pH-sensitive absorption spectrum and fluorescence yield decreases below pH 8 and the fluoresceins do not fluoresce at low pH.

Multiple fluorophores of different colors are used simultaneously in multi-parameter analyses for detecting and correlating different fluorescently-labeled materials in such procedures as flow cytometry, microscopy, chromatography and various other detection systems. In multi-parameter analyses, a number of fluorescent compounds having a binding affinity for different targets and having different maximum emission wavelengths are used to detect and quantify the sample's various targets. To reduce the overlap of fluorescence signals in multi-parameter analyses that are emitted from the target materials labeled with different fluorescent compounds, it is desirable to use fluorescent compounds with narrow absorption and emission bands.

One class of blue-fluorescing dyes, the coumarins, suffer from a number of disadvantages. For example, the coumarin-based fluorophore 7-amino-4-methylcoumarin acetate has broad absorption and emission peaks. Also, this compound has a relatively low extinction coefficient of approximately 17,000 l/mol-cm (Handbook, of Fluorescent Probes and Research Chemicals, Molecular Probes Inc., Eugene, Oreg.), thereby providing a fluorescence capacity (equal to the mathematical product of the extinction coefficient and the quantum yield) of approximately one-quarter that of the present inventions' compounds. Similarly, a fluorescent labeling dye available from Molecular Probes, Inc., under the trade name Cascade Blue (having the structure shown below where R is a reactive group) has an extinction coefficient of only 29,000 l/mol-cm.

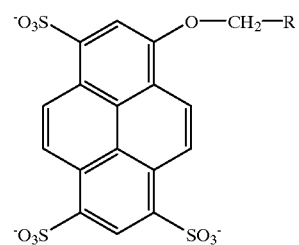

II

The cyanine compounds are now recognized as fluorescent labeling dyes. Cyanines generally include two heterocyclic groups connected by a chain of conjugated double bonds with an odd number of carbon atoms and have been used as spectral sensitizers for photographic film. Cyanine compounds are utilized as spectral sensitizers in, for example, U.S. Pat. Nos. 4,337,063 (Miraha et al.) and 4,404,289 (Masuda et al.), 4,405,711 (Masuda et al.), and British Patent No. 1,529,202 (Exekial et al.). Fluorescence is not necessary for the photographic applications in those patents and fluorescent properties are not mentioned in those patents. The utility of cyanine compounds as fluorescent dyes was discovered only recently.

Cyanine compounds known to be useful fluorescent dyes include the unrigidized, arylsulfonated cyanine compounds of U.S. Pat. No. 5,268,486 to Waggoner et al, having the following general structure:

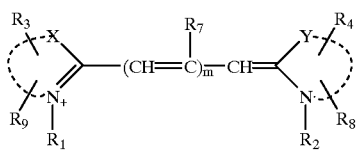

wherein, the dotted lines represent one to three rings having five to six atoms in each ring. $R_3$, $R_4$, $R_8$ and $R_9$ groups are attached to the rings. At least one of the $R_8$ and $R_9$ groups is a sulfonic acid or sulfonate group and at least one of the $R_1$, $R_2$, $R_3$, $R_4$ and $R_7$ groups is a moiety that will react with amino, hydroxy, phosphoryl, or sulfhydryl groups. The Waggoner et al. patent relates to trimethine, pentamethine, etc., cyanines (i.e., cyanines with more than a single double bond in the conjugated chain) and which fluoresce in the green, orange, red and near-infrared regions of the spectrum. Cyanines of this type have not been considered useful covalent labels.

One class of the cyanines includes a single atom bridging the heterocycles. These compounds are referred to herein as "rigidized" cyanines because the bridging atom restricts movement of the heterocycles about the conjugated carbon atom chain. Certain rigidized cyanines have been developed for photographic sensitization. See U.S. Pat. Nos. 2,541,400 to Brooker et al. and 3,148,187 to Heseltine. These cyanines cannot be used as fluorescent labeling dyes.

A group of rigidized cyanines having a single conjugated carbon atom linking the heterocyles ("rigidized monomethine cyanines") are those which are rigidized by incorporation of a boron molecule. Such compounds include pyrrole-based fluorophores derived from the bispyrromethene borondifluoride (2,2'-pyrromethene-1,1'-borondifluoride) complex having the following structure, where R represents various possible substituents:

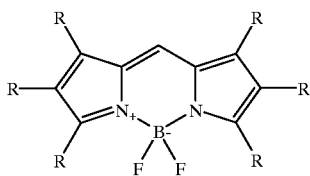

Particular derivatives of the bispyrromethene borondifluoride structure include 3,3',5,5'-tetramethyl-2,2'-pyrromethene-1,1'-boron-difluoride, sold under the trademark BODIPY by Molecular Probes, Inc., Eugene, Oreg. BODIPY analogs are disclosed in U.S. Pat. No. 4,774,339 to Haugland and Kang, as well as in "Handbook of Fluorescent Probes and Research Chemicals" compiled by Haugland and published by Molecular Probes, Inc. The application of pyrrole-based boron complexes as laser dyes and in photodynamic therapy is described in U.S. Pat. No. 4,916,711 to Boyer and Morgan. The lowest wavelength BODIPY molecule has been shown to have a maximum absorptive wavelength of 500 nm and a maximum emissive wavelength of 508 nm in aqueous media, i.e., in the "green" region of the spectrum. The synthetic scheme for producing the above pyrrole-based boron complexes is provided in Shah et al., "Pyrromethene-$BF_2$ Complexes as Laser Dyes", Heteroatom Chemistry, Vol. 1, Number 5 (1990) pages 389–399. Synthetic methods of the various boron complexes related to the BODIPY complexes are described in U.S. Pat. Nos. 4,774,339, 5,187,228, 5,248,782 and 5,274,113, all of Haugland et al.

The accepted general synthetic method for all bispyromethene boron complexes is shown below, where $R_1$ through $R_7$ are hydrogen or other groups or chromophores.

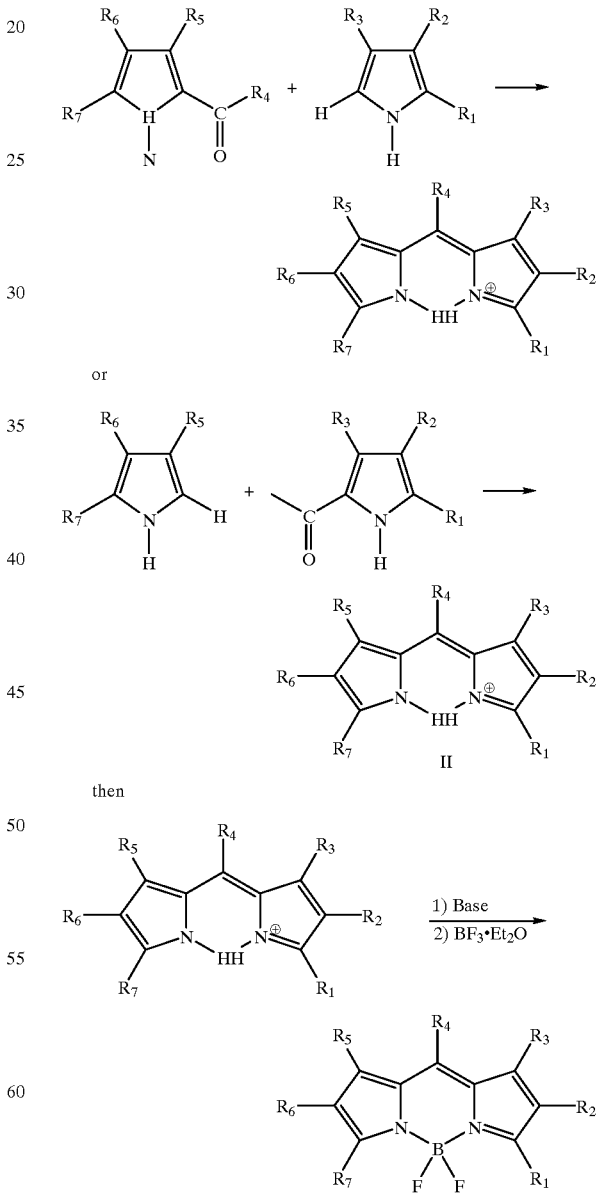

U.S. Pat. No. 4,774,339 describes pyrrole-based dyes which absorb and emit comparable to fluorescein, i.e., with maximum absorbance at approximately 490 nm and maximum emission at approximately 500 nm, and which include no additional chromophores attached to the basic structure shown in the general synthetic method above. U.S. Pat. No. 5,187,288 describes the synthesis of longer wavelength pyrrole-based boron complexes having additional chromophores at the $R_1$ and/or $R_6$ sites. Typical chromophores include phenylbutadienyl and phenylethenyl groups. U.S. Pat. No. 5,248,782 provides a synthetic method for longer wavelength pyrrole-based boron complexes dyes wherein heterocyclic bases are attached at $R_1$ and $R_6$. Typical examples of the heterocyclic bases include

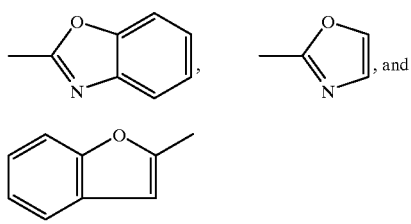

As disclosed in Kang and Haugland, "Spectral Properties of 4-Sulfonato-3,3'5,5'-Tetramethyl-2,2'-Pyrromethene-1,1'-Borondifluoride Complex (Bodipy), Its Sodium Salt, and Protein Derivatives", SPIE Vol. 1063 *New Technologies in Cytometry* (1989), pages 68–73, the BODIPY compound and its sulfonated derivative have the spectral properties provided in Table 1 and the sulfonated BODIPY derivative has the absorption and emission spectrum depicted in FIG. 1. The notation "RI" in Table 1 indicates that the values provided are relative intensities with 1.00 being the fluorescence intensity of the particular dye in methanol at the dye's maximum emissive wavelength.

TABLE 1

Spectral Data For BODIPY And Its Sulfonate Derivative

| Solvent | Max. absorption wavelength (nm) | Extinction coefficient ($cm^{-1}$ $mM^{-1}$) | Max. emission wavelength (nm) | RI |
|---|---|---|---|---|
| Bodipy-sulfonate: | | | | |
| Water | 494 | 39.7 | 509 | 0.67 |
| Methanol | 500 | 57.7 | 515 | 1.00 |
| Acetonitrile | 504 | 58.9 | 514 | 0.69 |
| Dioxane | 506 | 52.7 | 518 | 0.64 |
| Bodipy: | | | | |
| Water | 500 | — | 508 | 0.48 |
| Methanol | 501 | 85.3 | 509 | 1.00 |
| Acetonitrile | 501 | 86.7 | 508 | 0.87 |
| Dioxane | 505 | 80.0 | 512 | 0.63 |

A pyridine-based monomethine boron complex bis-benzomethene borondifluoride having the following structure

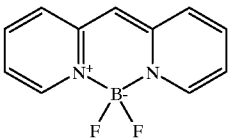

II was reported by Bashing, Schafer, and Steyer, Applied Physics, volume 3, p. 81 (1974). The synthetic scheme for producing the pyridine based compound is complex and was reported by Douglas (Journal of Heterocyclic Chemistry, Vol. 10, p. 255 (1973)).

Quinoline-based monomethine boron complexes having the following structures were reported by Scheibe and Daltrozzo, Advances in Heterocyclic Chemistry, volume 6, p. 153 (Academic Press 1965). However, their synthesis was never reported.

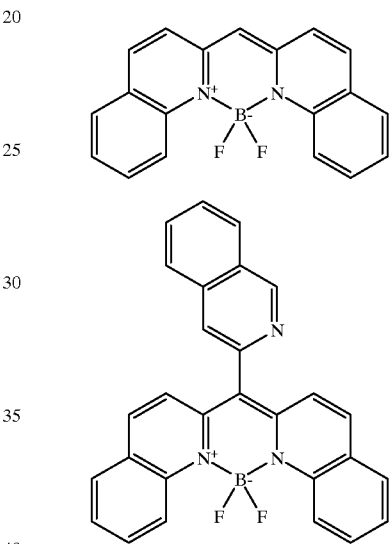

Although these quinoline-based compounds have been evaluated for use as laser dyes, it is unknown whether they are useful as fluorescent dye markers. Based on their structure, it is believed that the above quinoline-based molecules would have a maximum emissive wavelength significantly greater than 500 nm.

There is an absence of bright, soluble fluorescent dye compounds that fluoresce in the shorter wavelength (300–500 nm) region of the spectrum, have desirable spectral properties and can be used to impart fluorescence to a large number of materials. One object of the present invention is to provide a class of bright, highly fluorescent, strongly light-absorbing dyes that will emit in the spectrum's blue region, and that can be useful in a variety of biological and nonbiological applications. It is also an object of the invention to provide soluble fluorescent markers which have maximum absorptive and emissive wavelengths in the blue spectral region below 500 nm.

It is also an object of the present invention to provide fluorescent markers which can covalently or noncovalently label and/or detect biological and nonbiological materials such as, for example, enzymes and other proteins, amino acids, antibodies, drugs, hormones, nucleotides and polysaccharides.

It is also an object of the invention to provide pH-insensitive fluorescent markers having high quantum yields and extinction coefficients, and therefore high fluorescence, compared with available fluorescent markers.

It is a further object of the present invention to provide fluorescent markers which are relatively photostable, which have sharp and distinct absorption and emission maxima, and which have relatively small Stokes shifts.

An additional object of the present invention is to provide a fluorescent compound having a general chemical structure which is easily modified by the addition or substitution of chemical moieties to, for example, change the reactivity of the compound, modify the compound's emissive and absorptive maxima and solubility in polar or nonpolar solvents, and covalently or noncovalently associate the compound with a material.

SUMMARY OF THE INVENTION

To satisfy the above-stated objectives, the present invention relates to boron-rigidized monomethine cyanine complexes which can be prepared by the processes generally described below and which have the following structure:

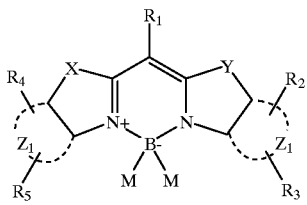

wherein M is selected from F and Cl and, groups $R_1$ through $R_5$ are chosen to provide desired solubility, reactivity, and spectral properties to the fluorescent compound. Such groups $R_1$ through $R_5$ include —P and —W—P wherein P may, for example, be selected from:

neutral groups that reduce water solubility selected from, for example, hydrogen and the halogen atoms;

polar groups that increase water solubility selected from, for example, amide, sulfonate, sulfate, phosphate, quaternary ammonium, hydroxyl and phosphonate;

functional groups that can be used in labeling reactions selected from, for example, amino, hydroxyl, sulfhydryl, carboxyl and carbonyl groups;

reactive groups selected from, for example, succinimidyl ester, isothiocyanate, isocyanate, iodoacetamide, maleimide, sulfonyl halide, phosphoramadite, alkylimidate, arylimidate, acid halide, substituted hydrazines, substituted hydroxylamines and carbodiimides; and electron donating and withdrawing groups that shift the absorption and emission wavelengths of the fluorescent molecule.

W is a linker chain of atoms and may be, for example, a straight or branched alkyl chain of 1–27 carbon atoms, monoethers containing 2–20 carbon atoms, and polyethers containing 2–20 carbon atoms.

More particularly, and with reference to the above figure, the boron-rigidized monomethine cyanine complexes of the present invention are those wherein:

M is selected from F and Cl;

X and Y are selected from $\geq C(CH_3)_2$, oxygen, sulfur, selenium, CH=CH, and N—W wherein N is nitrogen and W is selected from hydrogen, alkyl groups of twenty-six carbons or less, —$(CH_2)_n$P where 1<n<26 and P is selected from amino, aldehyde, acetal, ketal, halogen, cyano, aryl, heteroaryl, hydroxyl, sulfonate, sulfate, carboxylate, substituted amino, quaternary amino, nitro, substituted aryl, substituted heteroaryl, primary amide, substituted amide, and groups reactive with amino, hydroxyl, aldehyde, phosphoryl, or sulfhydryl groups;

dotted lines $Z_1$ and $Z_2$ represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur;

$R_2$, $R_3$, $R_4$ and $R_5$ are attached to the five-membered heteroatom rings including X and Y or, optionally, are attached to atoms of the $Z_1$ and $Z_2$ ring structures and each $R_2$, $R_3$, $R_4$ and $R_5$ is selected from hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, —E—F where F is hydroxy, sulfonate, sulfate, carboxylate, substituted amino or quaternary amino, and where E is a spacer group selected from —$(CH_2)_n$— where n is 0, 1, 2, 3, 4, or 5, and groups reactive with amino, hydroxyl, aldehyde, phosphoryl or sulfhydryl groups;

$R_1$ is selected from hydrogen, aryl, substituted aryl, heteroaryl, substituted heteroaryl, cyano, nitro, aldehyde, halogen, hydroxy, alkyl groups of twenty-six carbons or less, amino, quaternary amino, acetal, ketal, phosphoryl, sulfhydryl water-solubilizing groups, and —$(CH_2)_n$Q where 1<n<26 and Q is selected from amino, substituted amino, quaternary amino, aldehyde, acetal, ketal, halogen, cyano, aryl, substituted aryl, heteroaryl, substituted heteroaryl, hydroxyl, sulfonate, sulfate, carboxylate, amide, nitro, and groups reactive with amino, hydroxyl, aldehyde, phosphoryl, or sulfhydryl groups.

For particular applications such as laser dye applications, it may be desirable that each of $R_1$, $R_2$, $R_3$, $R_4$ and $R_5$ are hydrogen atoms. Therefore, the present invention is also directed to boron-rigidized monomethine cyanine complexes which have the following structure:

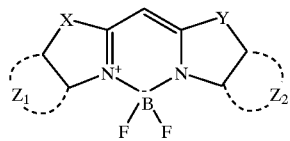

wherein:

X and Y are selected from carbon, oxygen, sulfur, selenium, CH=CH, and N;

dotted lines $Z_1$ and $Z_2$ represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur.

The structural differences between the compounds of the present invention and the nonrigidized cyanines are apparent. It has been found that monomethine cyanines tend to be non-fluorescent unless excited in an environment which maintains the molecule in a rigid posture. It is believed that thermal flexation of a monomethine cyanine's heterocyclic groups about the monomethine bridge may deactivate the molecule's excited state before fluorescence can occur. It has been found that rigidization of the cyanine structure results in greatly enhanced fluorescence without stearic hindrance of the numerous molecular positions available for the attachment of solubilizing, nucleophilic, reactive, or other groups. It is believed that rigidization between the heterocycles of the cyanine molecule inhibits the movement of the heterocycles about the bridging conjugated carbon atom when the molecule absorbs energy and a greater part of the energy absorbed by a rigidized molecule is re-emitted as light energy rather than heat relative to an unrigidized molecule.

The compounds of the present invention may be used in numerous biological and nonbiological applications. With respect to nonbiological applications, compounds of the present invention having one or more uncharged groups at the $R_1$ through $R_5$ positions, for example, alkyl and aryl moieties of twenty-six carbon atoms or less, may be dissolved in nonpolar materials to provide fluorescent properties to those materials. Such nonpolar materials include, for example, paints, polymers, waxes, oils, inks and hydrocarbon solvents. Another nonbiological application of the present invention is to dissolve compounds of the present invention having one or more charged and/or polar groups at the $R_1$ through $R_5$ positions in polar solvents or other materials such as, for example, water, ethylene glycol, methyl alcohol, or a mixture of water and methyl alcohol. Such charged R-groups include, for example, $-N^+$, $-SO_3^-$, $-PO_3^-$ and $-COO^-$, while such polar R-groups include, for example, hydroxyl groups. With respect to biological applications, biological molecules may be noncovalently labeled using the present invention's compounds. For example, compounds of the present invention wherein at least one of $R_1$ through $R_5$ are charged groups such as, for examples, amino and quaternary amino, may be used to noncovalently bind to charged biological molecules such as, for example, DNA and RNA. In addition, compounds of the present invention wherein at least one of $R_1$ through $R_5$ is an uncharged group such as, for example, a long chain alkyl, may be used to covalently bind to uncharged biological molecules such as, for example, biological lipids.

An additional application of the compounds of the present invention is the covalent labeling of a target material to impart fluorescent properties to the target material. Covalent labeling using the present invention's compounds may be either a biological or a nonbiological application depending on the particular application. Examples of target materials that may be covalently labeled in nonbiological applications include, for example, cellulose-based materials (including, for example, papers), textiles, petroleum-based products, photographic films, glasses, polymers and gel filtration and chromatography media.

Co-pending application Ser. No. 08/474,057 now U.S. Pat. No. 5,986,063, entitled "Monomethine Cyanines Rigidized by a Two-Carbon Chain," the entire disclosure of which is hereby incorporated by reference, provides one method for fluorescently labeling glass with a succinimidyl ester derivative of a monomethine cyanine compound having a two-carbon bridge rather than a boron bridge. The same method for glass labeling used in the foregoing co-pending application could be used with the compounds of the present invention. The first step of the glass labeling procedure may be, for example, the production of a succinimidyl ester derivative of a boron-rigidized compound of the present invention using the general method described in U.S. Pat. No. 5,268,486. The method of preparing the glass surface for binding by the fluorescent succinimidyl derivative of the boron-bridged compound would be the same as in the co-pending application.

Covalent labeling by the present invention's compounds may be accomplished in two ways. In a first procedure, a target material having at least one functional group selected from amino, hydroxyl, carbonyl, phosphoryl and sulfhydryl groups may be incubated with an amount of a compound of the present invention having at least one of $R_1$ through $R_5$ that is a reactive group that can covalently bind with the target material's functional group. The target material and the compound of the present invention are incubated under conditions and for a period of time sufficient to permit the reactive group of the fluorescent compound to covalently bond to the functional group of the target material. In an alternate procedure for imparting fluorescent properties to a target, an amount of a fluorescent compound of the present invention wherein at least one of $R_1$ through $R_5$ is a functional group selected from amino, hydroxyl, carbonyl, phosphoryl, carboxyl, and sulfhydryl groups is incubated with a target material having at least one reactive group that can covalently bind with the functional group of the fluorescent compound. The target material and the compound of the present invention are incubated under conditions and for a period of time sufficient to permit the reactive group of the target material to covalently bond to the functional group of the present invention's compound.

The compounds of the present invention can be structurally modified to react with different target compounds and/or to have different spectral properties, thereby providing a number of compounds which can be used in multi-parameter analyses wherein the presence and quantity of various compounds in a single sample must be differentiated based on the wavelengths and intensities of a number of detected fluorescence emissions. The pyrrole-based complexes described above access a longer wavelength region of the spectrum than the compounds of the present invention and have absorption and emission maxima at wavelengths significantly greater than those of the complexes of the present invention.

The boron-rigidized monomethine cyanine complexes of the present invention also have sharp and distinct absorption and emission maxima, a small Stokes shift, and are relatively photostable such that their emissive signals do not fade when they are illuminated in a detection system. For purposes of the present specification, the Stokes shift of a fluorescent compound is the absolute difference in nanometers between the compound's maximum absorptive and emissive wavelengths. Importantly, the boron complexes of the present invention may be synthesized by the methods disclosed herein. Derivatives of the compounds having a particular utility are prepared either by selecting appropriate precursors or by modifying the resultant compounds by known methods to include functional groups at a variety of positions. As examples, the complexes of the present invention may be modified to include certain reactive groups for preparing a fluorescent labeling reagent, or charged or polar groups may be added to enhance the solubility of the compound in polar or nonpolar solvents or materials.

The present invention also relates to labeling methods wherein boron-rigidized monomethine cyanine complexes of the present invention including at least one reactive group at the $R_1$ through $R_5$ positions covalently react with amino, hydroxyl, aldehyde, phosphoryl, carboxyl, sulfhydryl or other functional groups of proteins or other materials. (As used herein; a phosphoryl group comprises a phosphorous atom and a hydroxyl group linked thereto.) Such other materials which can be labeled by the compounds of the present invention include, but are not limited to, nucleic acid, DNA, RNA, blood cells, microbial materials, and drugs, toxins, particles, plastic or glass surfaces, polymers, and other materials which include amino, hydroxyl, aldehyde, phosphoryl or sulfhydryl reactive groups. Widely available automated DNA sequencers, capillary electrophoresis instruments and fluorescence gel readers are examples of instruments for detecting fluorecently labeled materials.

The present invention also relates to labeling methods wherein boron-rigidized monomethine cyanine complexes of the present invention including at least one functional group such as, for example, an amino, hydroxyl, aldehyde, phosphoryl, carboxyl, or sulfhydryl group, at the $R_1$ through $R_5$ positions covalently react with materials including at least one reactive group.

The compounds of the present invention may be made soluble in aqueous, other polar, or nonpolar media containing the material to be labeled by appropriate selection of R-groups.

In addition to the foregoing one-step labeling process, the present invention also relates to two-step labeling processes in which, in a first step, a compound of the present invention covalently reacts with and thereby labels a primary component, such as an antibody. In a second or staining step of the two-step procedure, the fluorescently labeled primary component is then used as a probe for a secondary component, such as an antigen for which the antibody is specific. When the target of the so-labeled antibodies is a cell, the second step of the procedure may be used to determine the amount of labeled antibodies which are attached to that type of cell by determining the intensity of the fluorescence of the cells. By this two-step procedure, monoclonal antibodies and other components covalently labeled in the first step with the fluorescent compounds of the present invention could be used as antigen probes.

The compounds of the present invention can also be used to determine the concentration of a particular protein or other component in a system. If the number of reactive groups on a protein which can react with a probe is known, the fluorescence per molecule can be known and the concentration of these molecules in the system can be determined by the total fluorescence intensity of the system. This particular method can be used to measure the concentration of various labeled analytes using microtitre plate readers or other known immunofluorescence detection systems. The concentration of fluorescently labeled material can also be determined using, for example, fluorescence polarization detection instruments.

The fluorescent compounds of the present invention can also be used in a detection method wherein a plurality of the fluorescent compounds are covalently attached to a plurality of different primary components, such as antibodies, each primary component being specific for a different secondary component, such as an antigen, in order to identify each of a plurality of secondary components in a mixture of the secondary components. According to this method of use, each of the primary components is separately labeled with a fluorescent compound having a different light absorption and emission wavelength compared with the dye molecules used for labeling the other primary components. The so-labeled primary components are then added to the preparation containing secondary components, such as antigens, and the primary components are allowed to attach to the respective secondary components for which they are selective. Any unreacted probe materials may be removed from the preparation by, for example, washing, to prevent interference with the analysis. The preparation is then subjected to a range of excitation wavelengths including the absorption wavelengths of particular fluorescent compounds. A fluorescence microscope or other fluorescence detection system, such as a flow cytometer or fluorescence spectrophotometer, having filters or monochromaters to select the rays of the excitation wavelength and to select the wavelengths of fluorescence is next employed to determine the intensity of the emission wavelengths corresponding to the fluorescent compounds utilized, the intensity of fluorescence indicating the quantity of the secondary component which has been bound with a particular labeled primary component. Known techniques for conducting multi-parameter fluorescence studies include, for example, multi-parameter flow cytometry.

In certain cases a single wavelength of excitation can be used to excite fluorescence from two or more materials in a mixture where each fluoresces at a different wavelength and the quantity of each labeled species can be measured by detecting its individual fluorescence intensity at its respective emission wavelength. If desired, a light absorption detection method can also be employed.

The detection method of the present invention can be applied to any system in which the creation of a fluorescent primary component is possible. For example, an appropriately reactive fluorescent compound can be conjugated to a DNA or RNA fragment and the resultant conjugate then caused to bind to a complementary target strand of DNA or RNA. Appropriate fluorescence detection equipment can then be employed to detect the presence of bound fluorescent conjugates.

The present invention also relates to the covalent reaction between compounds of the present invention and amine, hydroxy, aldehyde sulfhydryl, phosphoryl or other known functional groups on materials such as, for example, proteins, peptides, carbohydrates, nucleic acids, derivatized nucleic acids, lipids, certain other biological molecules, biological cells, soluble polymers, polymeric particles, polymer surfaces, polymer membranes, glass surfaces and other particles and surfaces. Because detecting fluorescence involves highly sensitive optical techniques, the presence of these dye "labels" can be detected and quantified even when the label is present in very low amounts. Thus, the dye labeling reagents can be used to measure the quantity of a material that has been labeled.

DETAILED DESCRIPTION OF THE INVENTION

The present invention relates to boron-rigidized monomethine cyanine complexes which have the following general structure:

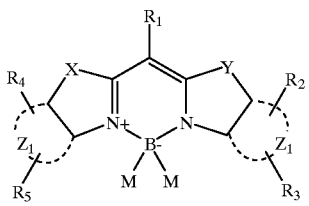

wherein X and Y are selected from carbon, $\geq C(CH_3)_2$, oxygen, sulfur, —CH=CH—, and —N—W wherein N is nitrogen and W is selected from hydrogen, alkyl groups of twenty-six carbons or less, —$(CH_2)_n$P where $1<n<26$ and P is selected from amino, aldehyde, acetal, ketal, halogen, cyano, aryl, heteroaryl, hydroxyl, sulfonate, sulfate, carboxylate, substituted amino, quaternary amino, nitro, substituted aryl, substituted heteroaryl, primary amide, substituted amide, and groups reactive with amino, hydroxyl, aldehyde, phosphoryl, carbonyl, or sulfhydryl groups. Dotted lines $Z_1$ and $Z_2$ represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur. $R_2$, $R_3$, $R_4$ and $R_5$ are attached to atoms of said $Z_1$ and $Z_2$ structures and each said $R_2$, $R_3$, $R_4$ and $R_5$ is selected from the group consisting of hydrogen, amino, quaternary amino, aldehyde, aryl, hydroxyl, phosphoryl, carbonyl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, —E—F where F is hydroxy, sulfonate, sulfate, carboxylate, substituted amino or quaternary amino, and where E is a spacer group selected from the group comprising —$(CH_2)_n$— where n is 0, 1, 2, 3, 4, or 5, and groups reactive with amino, hydroxyl, aldehyde, phosphoryl or sulfhydryl groups. $R_1$ is selected from hydrogen, aryl, substituted aryl, heteroaryl, substituted heteroaryl, cyano, nitro, aldehyde, halogen, hydroxy, alkyl groups of twenty-six carbons or less, amino, quaternary amino, acetal, ketal, phosphoryl, sulfhydryl, water-solubilizing groups, and —$(CH_2)_n$Q where $1<n<26$ and Q is selected from amino, substituted amino, quaternary amino, aldehyde, acetal, ketal, halogen, cyano, aryl, substituted aryl, heteroaryl, substituted heteroaryl, hydroxyl, sulfonate, sulfate, carboxylate, amide, nitro, and groups reactive with amino, hydroxyl, aldehyde, phosphoryl, or sulfhydryl groups. M is selected from F and Cl.

Groups $R_1$ through $R_5$ of the present invention can all be hydrogen so that there are no functional groups on those R positions. A compound with no functional groups in those positions would be useful for such applications as, for example, laser applications and additives in plastics.

The present invention also relates to bis-heteroaryl monomethine compounds that may be used, for example, as intermediates in the synthesis of the present invention's boron-rigidized monomethine cyanine compounds.

Figure 1:
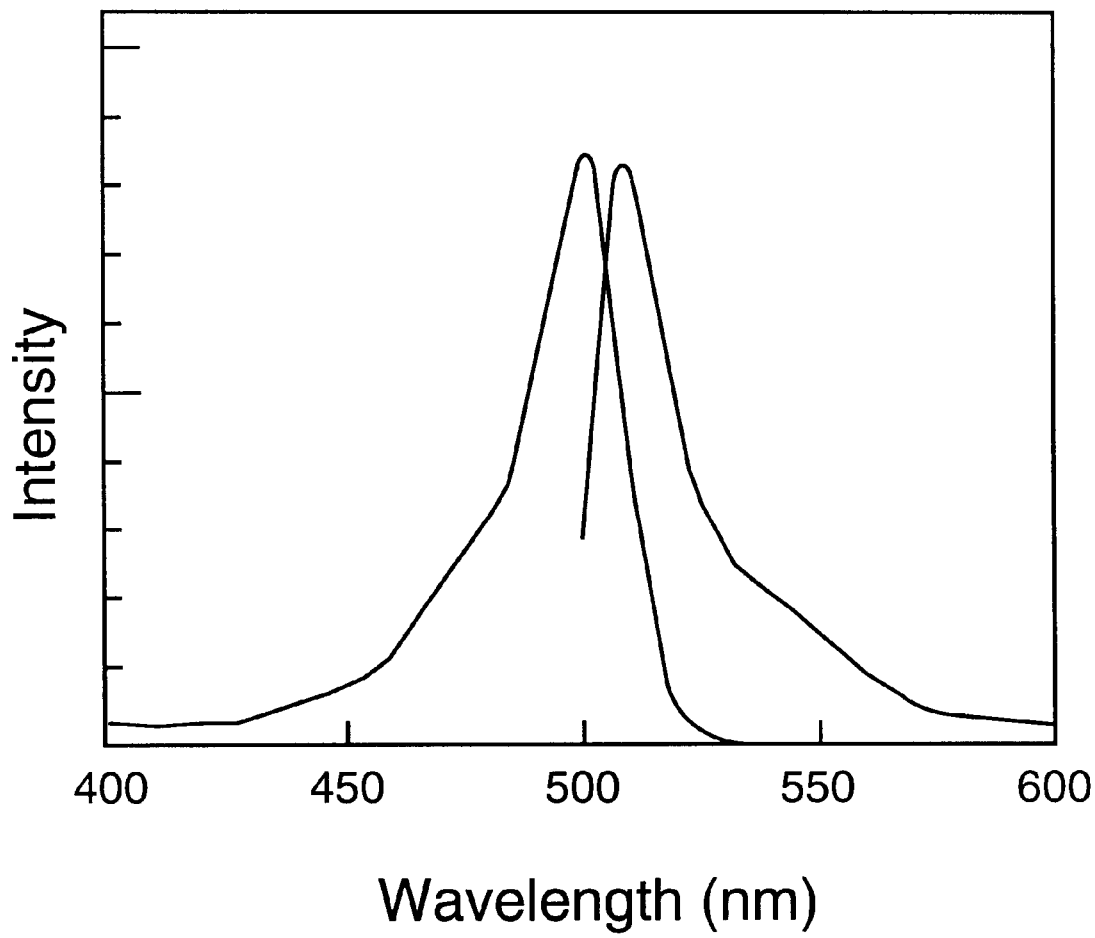
FIG. 1 is a plot of the absorption and emission spectra of the prior art Bodipysulfonate in methanol.
Figure 2:
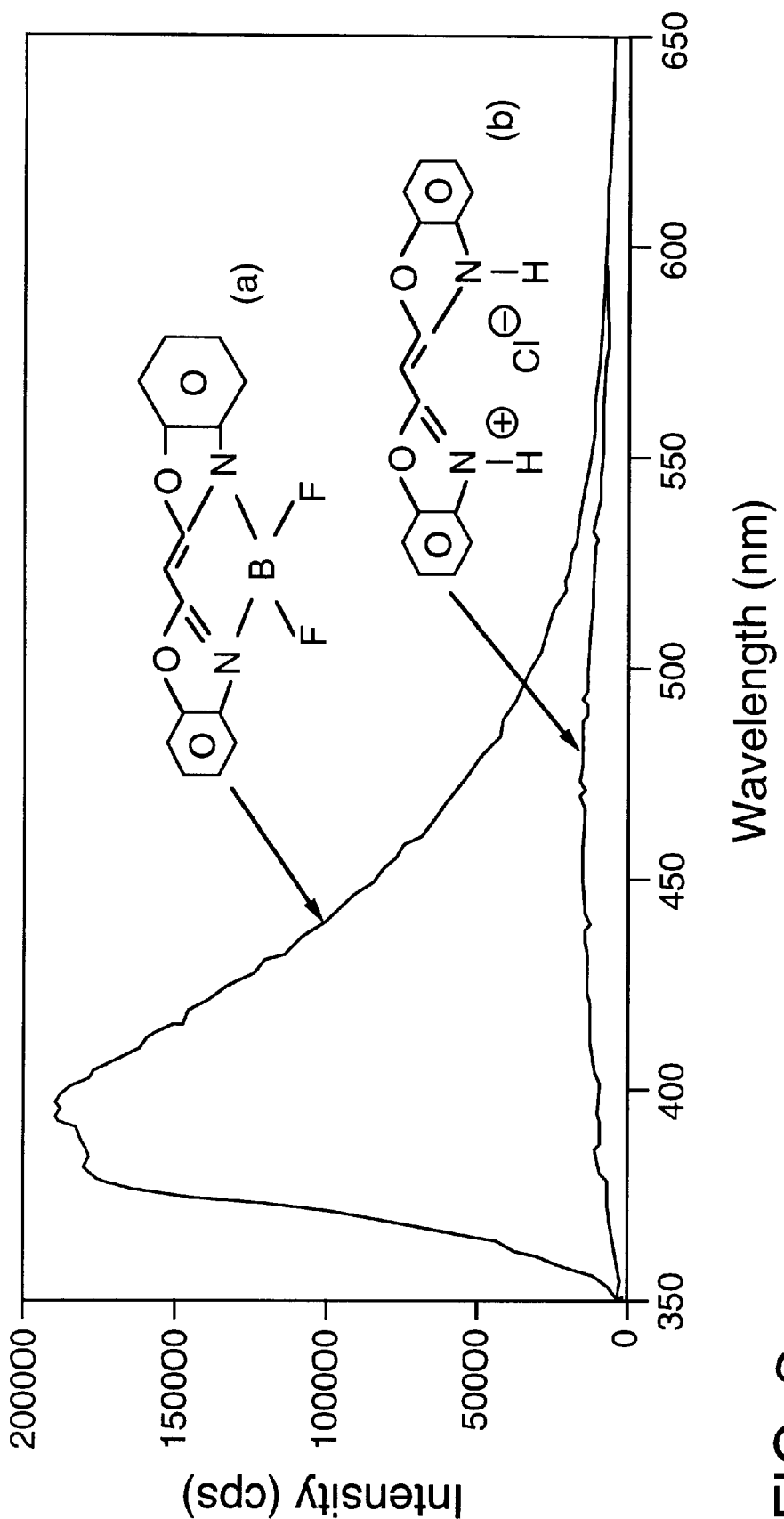
FIG. 2 is a plot of relative fluorescence intensity versus wavelength for bis-benzoxazolylmethene borondifluoride complex of the present invention and bis-benzoxazolylmethene hydrochloride.

The increase in fluorescence derived from rigidization of the heterocycles of the compounds of the present invention is demonstrated in FIG. 2 which shows the relative fluorescence spectra in methanol of bis-benzoxazolylmethene borondifluoride complex (curve a) and bis-benzoxazolylmethene hydrochloride (curve b), both excited at 348 nm. The quantum yield of the boron-rigidized complex is several fold greater than the unrigidized dye. The present inventors have determined that the rigidization of the basic monomethine cyanine structure increase the quantum efficiency of the dye molecules as much as 5 to 20 times. Thus, the boron-rigidized dyes of the present invention are unusually fluorescent compared with nonrigidized cyanine dye molecules. The present invention thus provides a method for increasing the fluorescence of dyes by rigidizing monomethine cyanine compounds with a boron bridge. Rigidization increase the planarity of the compound, and the fluorescence intensity.

Compared with, for example, the fluoresceins, the boron-rigidized monomethine cyanines of the present invention are particularly photostable and are insensitive to pH changes between pH 2 and pH 10. Certain of the compounds of the present invention maximally absorb and emit light at wavelengths between 400 and 500 nm or less and are therefore alternatives to conventional fluoresceins and rhodamines. Also, the present invention's approximate 400–500 nm emission maxima corresponds to the "blue" region of the visible spectrum and is therefore generally lower than the BODIPY compounds, quinoline-based monomethine cyanine complexes, and pyridine-based monomethine cyanine complexes discussed above, which have absorption and emission maxima of 500 nm or greater.

The present inventors believe that one of the determinants of a fluorescent molecule's maximum absorption and emissive wavelength, i.e., its "colors" of light absorption and fluorescence, may be the resonance distance established by the molecule's conjugated double bonds that lie between the two nitrogens that bind to the boron atom. Therefore, the 508 nm emission maximum of the prior art BODIPY molecule would result, in part, from its nine carbon atoms participating in the molecule's conjugated double bonds.

The present inventors have concluded that it is the number of conjugated double bonds and the corresponding resonance distance that is a major influence on the maximum absorption and emission wavelength of the fluorescent compound. It is believed that the shift to shorter absorption and emission wavelengths for the compounds of the present invention relative to the BODIPY compounds, the quinoline-based cyanine complexes and the pyridine-based complexes results from the relatively short resonance path of the present invention's compounds. Each of the prior art compounds has either five or six conjugated double bonds. The fluorescent molecules of the present invention, which have a sufficiently shorter resonance distance, i.e., two conjugated double bonds with three carbon atoms involved, provide a fluorescent molecule having absorptive and emissive maxima of significantly lower wavelengths than that of BODIPY and in the blue region of spectrum, that is to say in the wavelength region of 400–500 nm or less. These compounds, which have the favorable properties of cyanines (high extinction coefficient, high quantum yield, etc.) provide a highly desirable compound for fluorescence detection systems. The boron-rigidized monomethine cyanine complexes of the present invention are also highly fluorescent, having quantum yields greater than 0.5 and extinction coefficients approximating 90,000 liters/moles-centimeter.

The present inventors have also found that the maximum emissive wavelength of fluorescent cyanine compounds can be increased by attaching additional fused ring structures or heteroatoms to the cyanine's heterocycles. By slightly modifying the general chemical structure of the compound of the present invention, a number of fluorescent compounds may be provided having different maximum emission wavelengths over the entire visible spectrum. The different compounds can be used in multi-parameter fluorescence studies to detect the presence of numerous target molecules in a mixture. Each different marker will react with a different target and disclose the target's presence by fluorescing at a characteristic wavelength. Each different marker can include a group reactive with a different target substance or molecule.

The dyes of the present invention can also be used as laser dyes according to the procedures set forth in U.S. Pat. No. 4,916,711 to Boyer and Morgan. Laser dyes must be fluorescent, must have a quantum yield greater than 0.56 or 0.57 and must be reasonably photostable. The compounds of the present invention satisfy each of those requirements. Further, the dyes of the present invention can be used as textile dyes, photographic dyes and as organic conductors.

Specific examples of the groups which can be incorporated at the $R_1$, $R_2$, $R_3$, $R_4$, and $R_5$ sites of the present invention's compounds and the groups with which those R-groups will react are provided in Table 2. In the alternative, the functional groups listed in Table 2 can be incorporated at the $R_1$, $R_2$, $R_3$, $R_4$, and $R_5$ sites and would react with the listed corresponding reactive groups on the target.

TABLE 2

Possible Reactive Substituents and Sites Reactive Therewith

| Reactive Groups | Corresponding Functional Groups |
| --- | --- |
| succinimidyl esters | amines |
| anhydrides | amines, alcohols |
| acyl azides | amines |
| isothiocyanates | amines, thiols, alcohols, phenols |
| sulfonyl chlorides, sulfonyl fluorides | amines, phenols, alcohols |
| substituted hydrazines, substituted hydroxylamines | aldehydes, ketones |
| acid halides | amino groups |
| haloacetamides, maleimides | thiols, imidazoles, phenols, amines |
| carbodiimides | carboxyl groups |
| phosphoramidite | alcohol groups |

In addition to those groups listed in Table 2, a number of other possible groups for the present invention's $R_1$, $R_2$, $R_3$, $R_4$, and $R_5$ sites exist. For example, the reactive groups which are especially useful for labeling target components with available amino and hydroxy functional groups include:

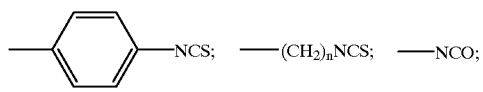
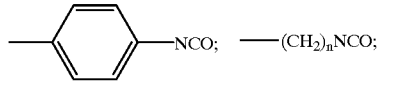
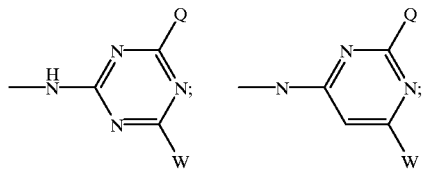
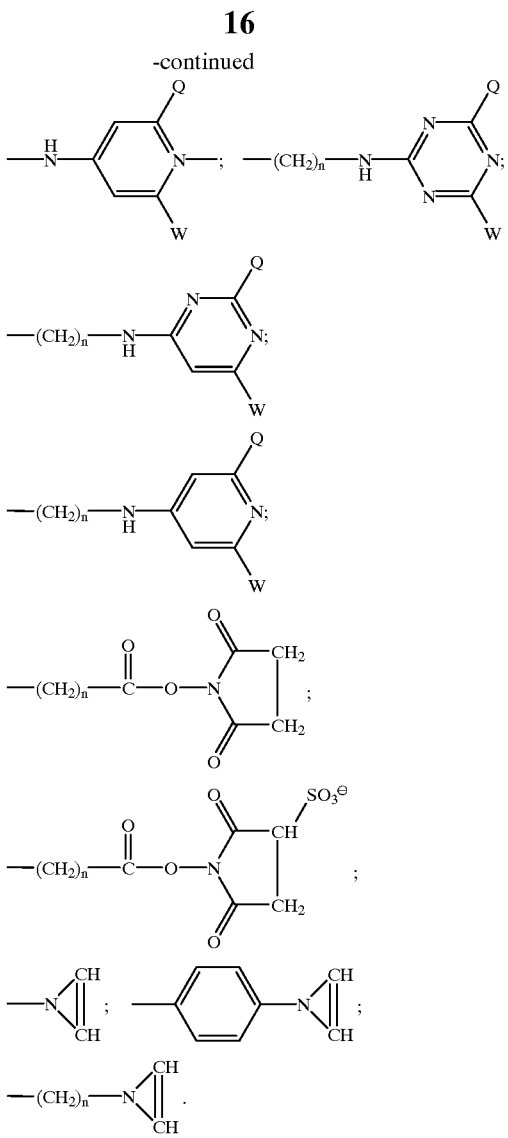

where at least one of Q or W is a leaving group such as I, Br, Cl.

Specific examples of possible $R_1$, $R_2$, $R_3$, $R_4$, and $R_5$ groups that are especially useful for labeling target components with available sulfhydryl functional groups include:

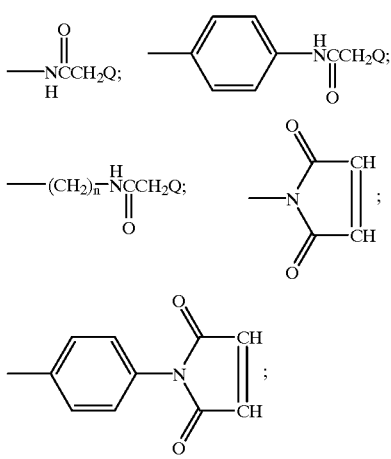

-continued where Q is a leaving group such as I or Br,

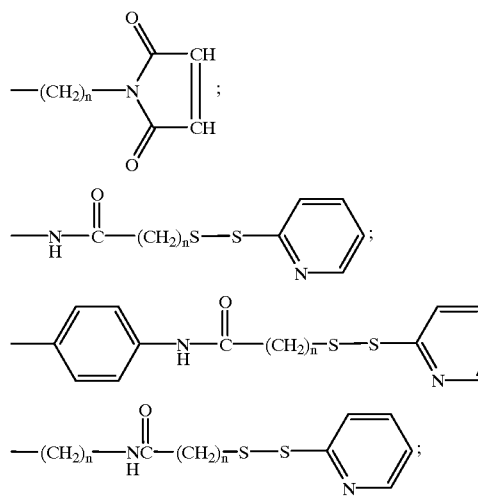

where n is 0 or an integer.

Specific examples of possible $R_1$, $R_2$, $R_3$, $R_4$, $R_5$ functional groups that are especially useful for labeling target components by light-activated cross linking include:

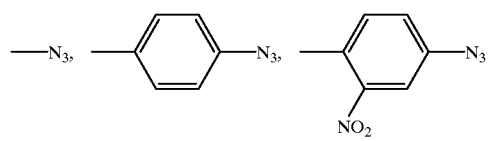

For the purpose of increasing water solubility or reducing unwanted nonspecific binding of the fluorescently-labeled component to inappropriate components in the sample or to reduce interactions between two or more reactive chromophores on the labeled component which might lead to quenching of fluorescence, the $R_1$, $R_2$, $R_3$, $R_4$, and $R_5$ functional groups can be selected from the well known polar and electrically charged chemical groups. Examples of such groups are —E—F where F is hydroxy, sulfonate, sulfate, carboxylate, substituted amino or quaternary amino, and where E is a spacer group such as —$(CH_2)_n$— where n is 0, 1, 2, 3, or 4. Useful examples of —E—F groups include lower alkyl and alkyl sulfonates, such as —$(CH_2)_3$—$SO^-$ and —$(CH_2)_4$—$SO_3^-$.

The groups provided herein are not meant to be all-inclusive of those groups which can be incorporated at the R sites of the compounds of the present invention. It will be understood that there are various other groups which will react with groups on material that is to be labeled by the compounds of the present invention. Compounds produced by the incorporation of such other groups at the $R_1$ through $R_5$ positions are intended to be encompassed by the present invention.

There are two general schemes for preparing the monomethine cyanine boron complexes of the present invention. A separate synthesis scheme is necessary for both the symmetric and the asymmetric boron-rigidized compounds of the present invention.

Preparation of the Symmetric Dyes

The general synthetic scheme for preparing the symmetric dyes, i.e., those dyes having heterocyclic groups which are identical, is as follows:

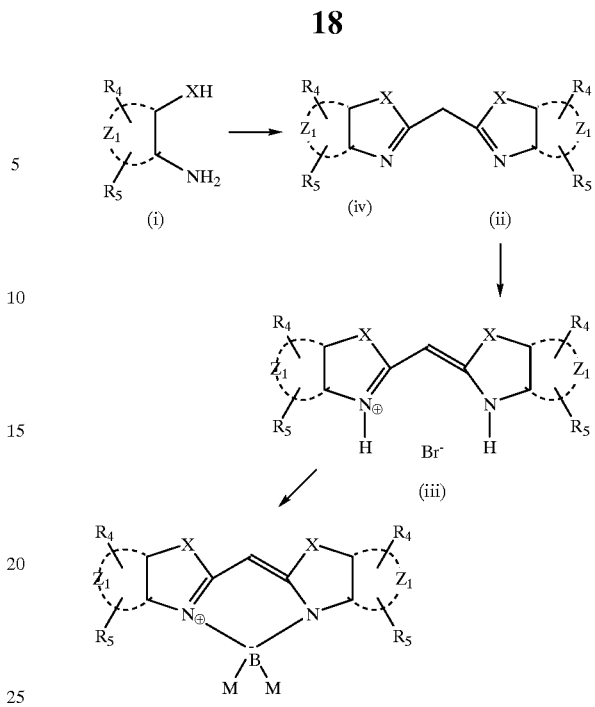

Depending on the final structure desired, the X substituent of the starting material (i) is selected from among —$C(CH_3)_2$, sulfur, oxygen, —CH=CH— and N—W where N is nitrogen and W is selected from hydrogen, alkyl, aryl and heteroaryl and other functional groups and $Z_1$, $R_4$ and $R_5$ are selected from those structures and groups listed for $Z_1$, $R_4$ and $R_5$ above. In general, in the above synthetic method for producing the symmetric boron-rigidized monomethine cyanine compounds of the present invention, the starting material (i) undergoes a cyclocondensation reaction in the presence of heat and at least one compound selected from $CH_2(CN)_2$, $CH_2(COOH)_2$ and $CH_2(COOEt)_2$ to provide a bis product (ii) which includes two linked units of heterocyclic moiety (i). In the alternative, starting material may undergo the cyclocondensation reaction to produce bis product (ii) by the addition, in the presence of heat, of

I

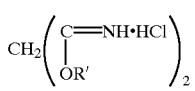

wherein R' is selected from methyl, ethyl, n-butyl, and propyl.

The bis product (ii) may then be quaternized in the presence of hydrobromic acid so as to produce the quaternary monohydrobromide salt structure (iii). Other acids, for example, such as $HClO_4$, paratoluene sulfonic acid, $CF_3COO^-$ can also be used. The cyclocondensation reaction combines similar molecules, with the elimination of water, alcohol, or $NH_3$, to form a bis-methylene complex compound. The quaternization reaction establishes conjugation between the nitrogen atoms. However, depending on the substituent on the center carbon, the conjugation can be established without treatment by HBr or other acid. Finally, the monohydrobromide salt (iii) undergoes condensation by addition of at least one of the boron compounds $BM_3$, (where M is one of the halogen atoms F, Cl, Br and I), preferably boron trifluoride etherate, in the presence of an organic base such as N,N diisopropylethyl-amine in a solvent such as toluene. Solvents with low polarity are also preferred. Organic base serves two functions. First, it extracts the acid HBr from the quaternary salt to generate, in situ, a somewhat unstable enamine tautomer species (wherein conjugation is established between the nitrogen atoms) of the active bis-methylene compound.

Following the addition of the boron compound a coordination complex (iv) between the enamine tautomer and the boron atom is formed. In the process, one molecule of HF is eliminated and quickly neutralized by the excess organic base (N,N diisopropylethyl-amine). This neutralization step is the second function for the base.

Previous literature work has shown that the equilibrium between the bis-methylene compound and its tautomer is influenced by the basicity of the heterocyclic moiety as well as the substituent on the center carbon atom. An electron withdrawing substituent, for example, will make the hydrogen atom very acidic, thus shifting equilibrium in favor of the enamine tautomer. In such case, the quaternization step can be skipped (as shown in Example G below).

This final step produces the symmetric boron-bridged monomethine cyanine complexes (iv) of the starting units (i). The foregoing reactions are preferably conducted at approximately 100–125° C., and each reaction step is preferably allowed to progress for 15 minute to 1 hour. A more specific example of the present invention's method for producing the symmetric intermediate bis compounds (ii) and the symmetric final boron complex (iv) shown above follows.

The synthesis method disclosed for producing the pyrrole-based boron complexes, such as BODIPY described above, cannot be used to create the boron complexes of the present invention.

In one embodiment of the present invention's method for producing a symmetric bis compound, in a first step a precursor is provided having the following structure:

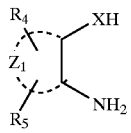

wherein $Z_1$, $R_4$ and $R_5$ are selected from those groups and structures for $Z_1$, $R_4$ and $R_5$ listed above.

In the next step, the precursor of the first step is reacted in the presence of heat with at least one reactant selected from $CH_2(CN)_2$, $CH_2(COOH)_2$, $CH_2(COOEt)_2$ and

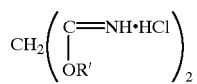

I where R' is selected from methyl, ethyl, propyl and n-butyl, to provide a symmetrical bis-heteroaryl methane compound having the structure

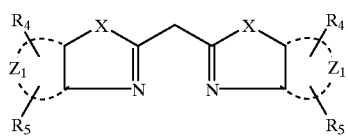

The bis-heteroaryl methane compound may be further processed to provide a boron-rigidized monomethine compound of the present invention. To produce the boron-rigidized monomethine compound, in a third step, the symmetrical bis-heteroaryl compound of step two is quaternized in the presence of an acid, preferably selected from para-toluene sulfonic, acid, HBr, $CF_3COOH$ and $HClO_4$, to provide a monoquaternary salt of the symmetrical bis-heteroaryl compound having the following structure:

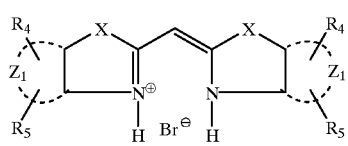

In a fourth step, the monoquaternary salt of the symmetrical bis-heteroaryl compound is condensed in the presence of organic base by addition of a compound selected from $BM_3$ where M is selected from the halogen atoms F and Cl, preferably boron trifluoride etherate, to provide a boron-rigidized monomethine compound having the structure

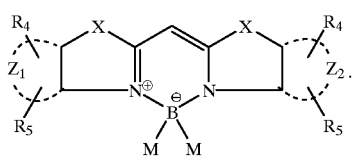

Preparation of the Asymmetric Dyes

The general synthetic scheme for preparing the asymmetric dyes, i.e., those dyes having heterocyclic groups which are different, is as follows:

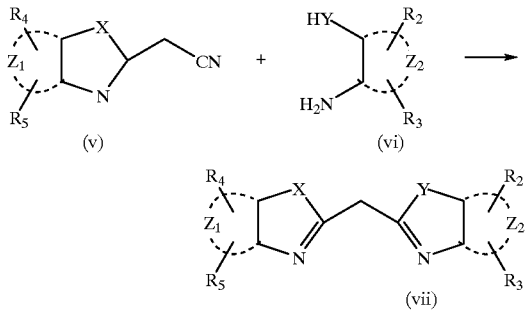

-continued

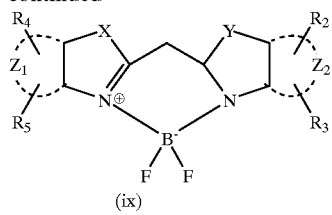

(ix)

It will be seen that the steps of quaternization by hydrobromic acid and the condensation by borontrifluoride are identical to that for producing the symmetric compound. However, the initial step of linking precursors (v) and (vi) to provide compound (vii) differs from that of the synthetic pathway for the symmetric product. Precursor compounds of chemical formula (v) can be prepared from aromatic amine compounds by the method described in U.S. Pat. No. 4,064,136 to Loew et al., the entire disclosure of which is hereby incorporated by reference.

A more specific example of the present invention's method for producing the asymmetric intermediate bis compounds (vii) and the asymmetric final boron complex (ix) shown above follows. Initially, a precursor is provided having the following structure

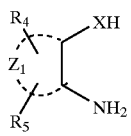

wherein $Z_1$, $R_4$ and $R_5$ are selected from those groups or structures listed above for $Z_1$, $R_4$ and $R_5$.

The precursor is reacted in appropriate stoichiometry with

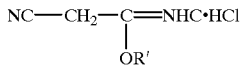

where R' is selected from methyl, ethyl, n-butyl, and propyl, to provide a first intermediate compound having the structure (v)

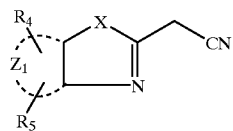

(v)

Next, the intermediate compound (v) is reacted with HCl and at least one compound selected from methanol, ethanol, propanol and butanol to provide an intermediate compound (va) having the structure

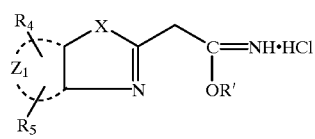

(va)

The intermediate (va) is reacted in methanol or ethanol solvent with a second precursor compound having the structure

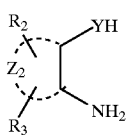

(vi)

wherein Y, $Z_2$, $R_2$ and $R_3$ are selected from the groups and structures provided above for those positions, to provide an asymmetrical bis-heterocyclic methane compound having the structure

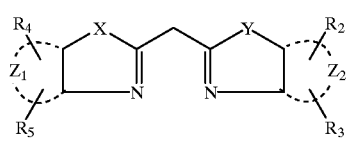

(vii)

Although the above method refers to the production of an asymmetric bis-heterocyclic methane compound, it will be understood that by proper selection of $R_2$ through $R_5$, a symmetric bis-heteroaryl methane compound can also be produced. The symmetric or asymmetric bis-heterocyclic methane compound produced by the foregoing method may be further processed to provide asymmetric or asymmetric boron-rigidized monomethine compound, respectively. To produce the boron-rigidized monomethine compound, the symmetric or asymmetric bis-heterocyclic compound of step four is quaternized in the presence of an acid, preferably selected from paratoluene sulfonic acid, HBr, $CF_3COOH$ and $HClO_4$, to provide a monoquaternary salt of the bis-heterocyclic compound having the following structure:

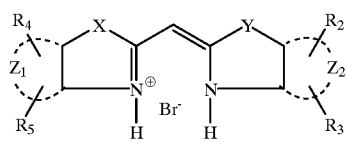

(viii)

The monoquaternary salt is then condensed in the presence of base by the addition of boron trifluoride etherate to provide a boron-rigidized monomethine compound having the structure

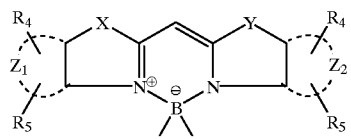

To provide selected groups at the $R_1$ through $R_5$ sites of the present invention's boron-rigidized monomethine cyanine complexes, selected precursors may be employed in the foregoing synthetic pathways. Alternatively, the boron-rigidized complexes can be modified after they are produced to include groups at the R-sites by well known chemical techniques including, for example, sulfonation, nitration, alkylation, acylation, and halogenation. Furthermore, the complexes can be further modified to introduce chemically reactive groups that are understood to fall within the scope of this invention.

$R_1$ Group Incorporation

The present invention also provides a method to modify a bis-heteroaryl compound produced by any of the foregoing methods to include a group at the $R_1$ position, i.e., at the carbon of the conjugated monomethine chain linking the heterocycles. In a first step of the method, a bis-heteroaryl compound is provide having the structure

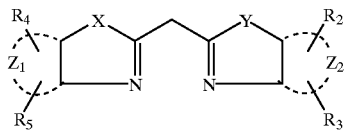

where X, Y, $Z_1$, $Z_2$ and $R_2$ through $R_5$ are selected from those structures and groups provided above for those positions.

The bis-heteroaryl compound of step 1 may be provided by, for example, the methods of the present invention discussed above.

In a second step, the bis-heterocyclic compound of step 1 (a) is reacted in appropriate stoichiometry and in the presence of a compound selected from NaH, NaOMe, and NaOEt, with a compound G-$R_1$ where G is selected from chlorine, bromine and iodine and $R_1$ is selected from hydrogen, aryl, substituted aryl, heteroaryl, substituted heteroaryl, cyano, nitro, aldehyde, halogen, hydroxy, alkyl groups of twenty-six carbons or less, amino, quaternary amino, acetal, ketal, phosphoryl, sulfhydryl, water-solubilizing groups, and —$(CH_2)_nP$ where $1<n<26$ and P is selected from those groups described earlier for P to provide a bis-heterocyclic methane compound having the structure

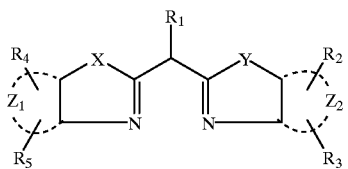

The bis-heterocyclic methane compound of step 2 may be further reacted by the quaternization and condensation steps discussed above to provide a boron-rigidized monomethine cyanine compound having the following structure:

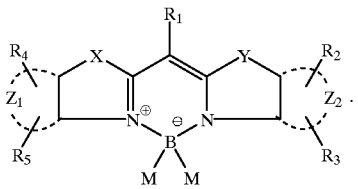

Several examples of symmetric boron-rigidized monomethine cyanine complexes that can be synthesized using the symmetric compound synthetic scheme schematically illustrated above are provided below.

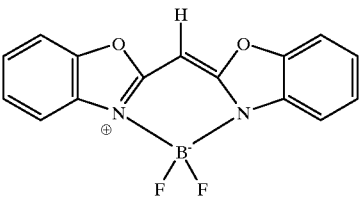

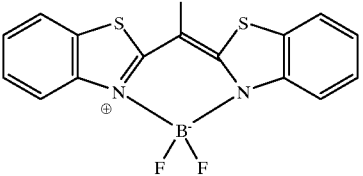

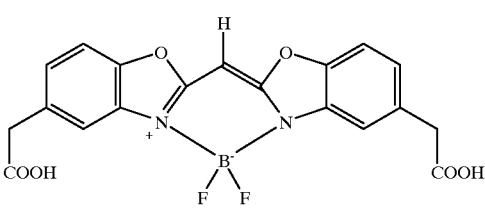

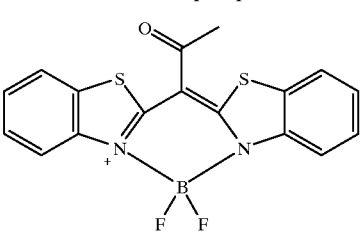

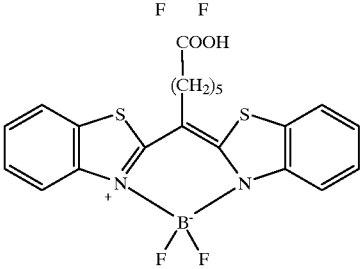

Several examples of asymmetric boron-rigidized monomethine cyanine complexes that can be synthesized using the asymmetric compound synthetic scheme schematically illustrated above are provided below.

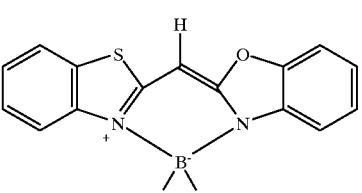

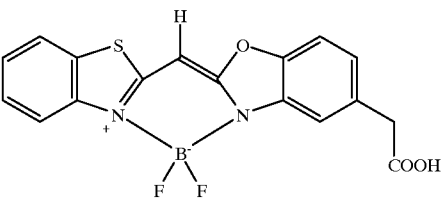

-continued

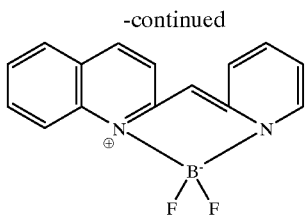

Following are specific examples of the synthesis of compounds of the present invention and observed spectral data for those compounds.

Example A

Bis-benzothiazolylmethene borondifluoride

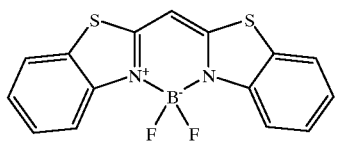

To produce the above compound, in a two-neck 100 ml round bottom flask with a condenser and a stir bar, malononitrile (2.64 g, 40 mmol) was dissolved in absolute ethanol (40 ml). 2-amino thiophenol (10 g, 80 mmol) was slowly added to this solution under stirring. Under a nitrogen blanket, the reaction mixture was heated and refluxed for six hours. After cooling, the flask was refrigerated overnight. Pale green crystals of bis(2-benzothiazolyl) methane that formed were recovered following vacuum filtration, washing with hexane and drying (yield: 82%). 2.82 g (10 mmol) of the bis(2-benzothiazolyl) methane was dissolved in chloroform (50 ml) in an erlenmeyer flask. Hydrobromic acid (10 mmol) in glacial acetic acid was added dropwise with gentle stirring. A canary yellow precipitate formed within minutes, causing thickening of the reaction mixture. Stirring was continued for one hour at room temperature. A fine yellow powder was recovered, following filtration and washing with ether. The yield was quantitative and the bis(2-benzothiazolyl) methane monohydrobromide product was sufficiently pure to be used in the next step.

1.1 g (3 mmol) of the bis(2-benzothiazolyl) methane mono hydrobromide was suspended in dry toluene (50 ml) in a round bottom flask fitted with a stir bar. Then N,N disopropyl ethyl amine (1.6 ml, 9 mmol) was added slowly to the suspension under stirring. The suspension became clear and colorless. Using a syringe, boron trifluoride etherate (1.1 ml, 9 mmol) was added carefully to the clear solution. The reaction mixture turned immediately yellow and some solid separated out. Under a nitrogen atmosphere, the flask was heated on a steam bath for one hour, cooled, and the contents quenched with water (50 ml). The toluene layer was separated and stored in a refrigerator to separate out a small quantity of yellow solid. The toluene layer was then filtered and the filtrate was evaporated on a rotary evaporator to again yield a yellow solid that was redissolved in acetone (20 ml). Solid material insoluble in acetone was filtered and the desired bis(2-benzothiazolyl) methene boron difluoride complex crystallized from the filtrate (yield: 80%)

Example B

Bis-benzoxazolylmethene borondifluoride

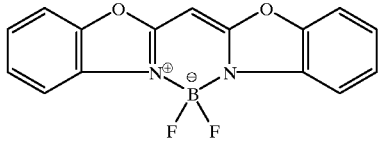

To produce the above compound, ortho aminophenol is condensed with malonic acid in polyphosphoric acid medium to produce bis (2-benzoxazolyl) methane in a 32% yield. See U.S. Pat. No. 3,250,780, the disclosure of which is incorporated herein by reference. An alternative to malonic acid in the condensation reaction is malonic acid diester. The condensate is then quaternized as in Example A and is subsequently condensed as in Example A above to form the boron-rigidized complex.

The observed absorption maxima, molar extinction coefficients, emission maxima and qualitative solubility data for the boron-rigidized complexes of Examples A and B are provided in Table 3.

TABLE 3

Spectral and Solubility Data for the Compounds of Examples A and B

| | Bis-benzothiazolyl borondifluoride | | | Bis-benzoxazolyl borondifluoride | | | |
|---|---|---|---|---|---|---|---|
| Solvent | Max. absorption wavelength (nm) | Logarithm of the Extinction coefficient ($M^{-1}$ $cm^{-1}$) | Max. emission wavelength (nm) | Max. absorption wavelength (nm) | Logarithm of the Extinction coefficient ($M^{-1}$ $cm^{-1}$) | Max. emission wavelength (nm) | Solubility data* (qualitative) |
| Methanol | 418 | — | 422 | 358 | — | 385 | sparingly sol. |
| Ethanol | 418 | — | 423 | 358 | — | 386 | sparingly sol. |
| Acetonitrile | 418 | 4.97 | 423 | 358 | 4.72 | 385 | sol. |
| Ethyl Acetate | 418 | 4.98 | 423 | 358 | 4.74 | 383 | sol. |

TABLE 3-continued

Spectral and Solubility Data for the Compounds of Examples A and B

| | Bis-benzothiazolyl borondifluoride | | | Bis-benzoxazolyl borondifluoride | | | |
| --- | --- | --- | --- | --- | --- | --- | --- |
| Solvent | Max. absorption wavelength (nm) | Logarithm of the Extinction coefficient ($M^{-1}$ $cm^{-1}$) | Max. emission wavelength (nm) | Max. absorption wavelength (nm) | Logarithm of the Extinction coefficient ($M^{-1}$ $cm^{-1}$) | Max. emission wavelength (nm) | Solubility data* (qualitative) |
| Chloroform | 420 | 4.97 | 425 | 360 | 4.72 | 386 | sol. |
| Toluene | 420 | 4.95 | 427 | 360 | 4.74 | 392 | sol. |

*Solubility data applies to either dye compound in the indicated solvent.

The absorption maxima of the boron-rigidized complexes lie in the blue region, with the oxazole-based compound absorbing ultraviolet light and the thiazole-based compound absorbing blue light. The absorption and emission maximal are practically insensitive over a wide range of solvent polarity. Both compounds have relatively small Stokes shifts, the oxazole-based compound having a 28 nm shift and the thiazole-based compound having only a 5–7 nm shift. It is believed that smaller Stokes shifts are characteristic of compounds wherein the radiative process, i.e., the emission of photons, is the dominant mode by which absorbed energy is dissipated. Smaller Stokes shifts also characterize compounds having low triplet-triplet absorption. The molar extinction coefficients reported in Table 3 for the compounds of Examples A and B are amongst the highest observed for blue emitting dyes.

Figure 3:
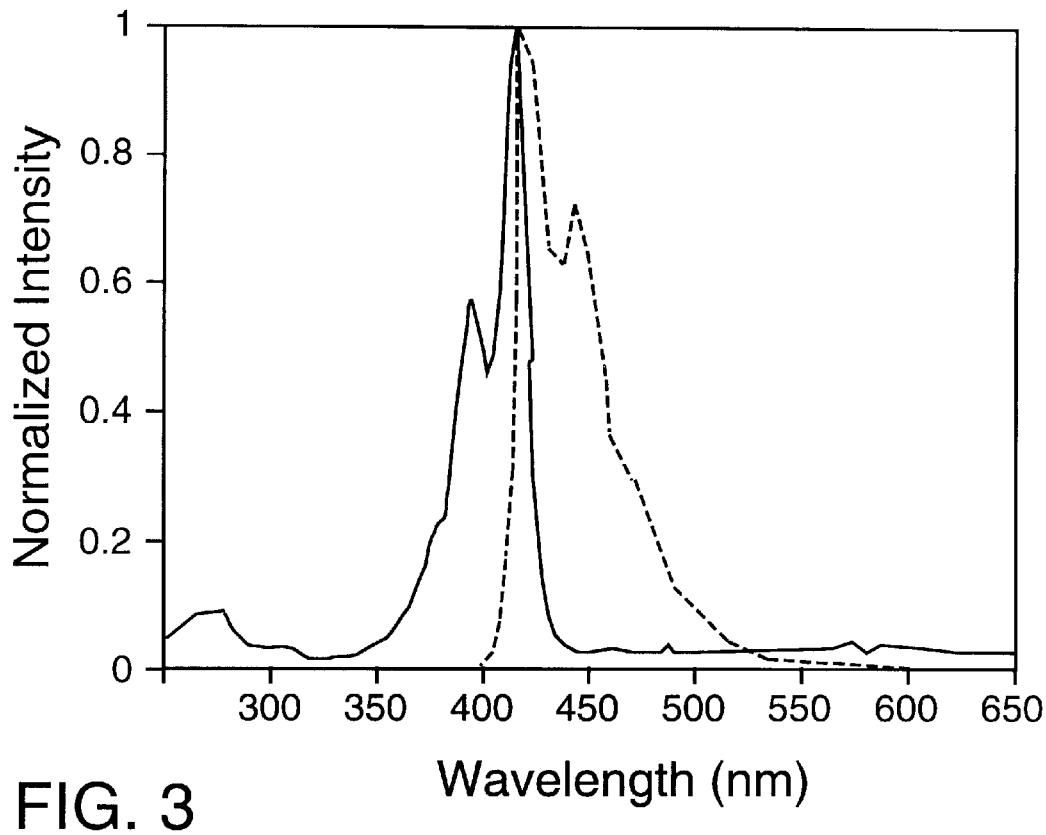
FIG. 3 is a plot of the absorption and emission spectra of bis-benzothiazolylmethene borondifluoride compound of the present invention.
Figure 4:
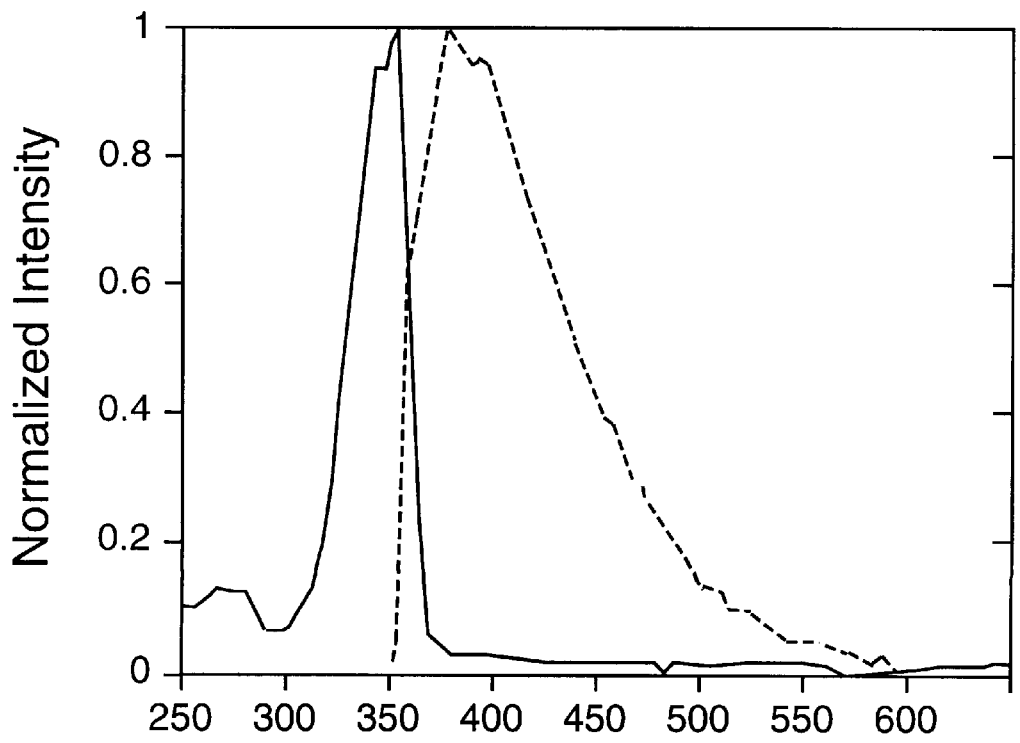
FIG. 4 is a plot of the absorption and emission spectra of bis-benzoxazolylmethene borondifluoride compound of the present invention.

As shown in FIG. 3 (thiazole compound of Example A) and FIG. 4 (oxazole compound of Example B), the absorption spectra (solid line) and emission (dotted line) spectra for the compounds are characterized by sharp and narrow absorption peaks and emission peaks which are somewhat broader. The full width at half maximum absorption are only half those of Coumarin-type dyes with similar absorption maxima. While the emission spectrum of the thiazole compound of Example B mirrors its absorption spectrum, the emission spectrum of the oxazole compound of Example A appears to be much broader. This is believed to be unusual because the shape of the fluorescence emission spectrum typically mirrors the shape of the absorption spectrum. Therefore, considering the similarity in structure between the oxazole and thiazole compounds of Examples A and B, the observed emission spectrum of the oxazole compound is unexpected.

Relative fluorescence intensities of the compounds of Examples A and B in a variety of solvents are provided in Table 4. Table 4 indicates that the fluorescence intensities of the dyes are insensitive to solvent polarity. Extremely high fluorescent quantum efficiencies also were observed for both dye compounds, resulting at least in part from the increased rigidity of the compounds due to their complexation by boron difluoride and the planar nature of the synthesized molecules. Chemical structure analysis has indicated that the dihedral angle between the planes of the two heterocyclic wings on each side of the center carbon atom is less than 5° for bis-benzothiazolyl methene boron complex. See M. T. Ramos et al., *Heterocycles*, Vol. 29, p. 165 (1989).

TABLE 4

Fluorescence Intensity Data for the Compound of Example A and B

| Solvent | Bis-Benzothiazolylmethene Borondifluoride | Bis-Benzoxazolylmethene Borondifluoride |
| --- | --- | --- |
| Methanol | 0.89 | 1.35 |
| Ethanol | — | 1.33 |
| Acetonitrile | 0.89 | 1.39 |
| Ethyl Acetate | 0.97 | 1.20 |
| Chloroform | 0.91 | 1.27 |
| Toluene | 0.81 | 1.42 |

The resistance to photodegradation of the compounds of Examples A and B in methanol and dichloromethane was also investigated and was compared with photofading rates of certain Coumarin dyes. A degassed solution of each dye in a quartz cuvette was illuminated with a 500 watt mercury vapor lamp from a distance of 4 inches. The solution optical density at maximum wavelength was monitored as a function of time. In methanol, the oxazole-based compound and the corresponding Coumarin compound faded at a similar rate, while the thiazole-based compound faded somewhat faster. In dichloromethane, both the oxazole and thiazole based compounds exhibited a small red shift (approximately 12 nm) at the maximum wavelength. The Coumarin dyes also exhibited shifts in maximum wavelength. The compounds of Examples A and B in dichloromethane were also more resistant to photofading than the Coumarin dyes.

Example C

Bis-carboxymethyl Benzoxazolylmethene Borondifluoride

The synthetic pathway for this compound is a eight-step procedure schematically represented as follows.

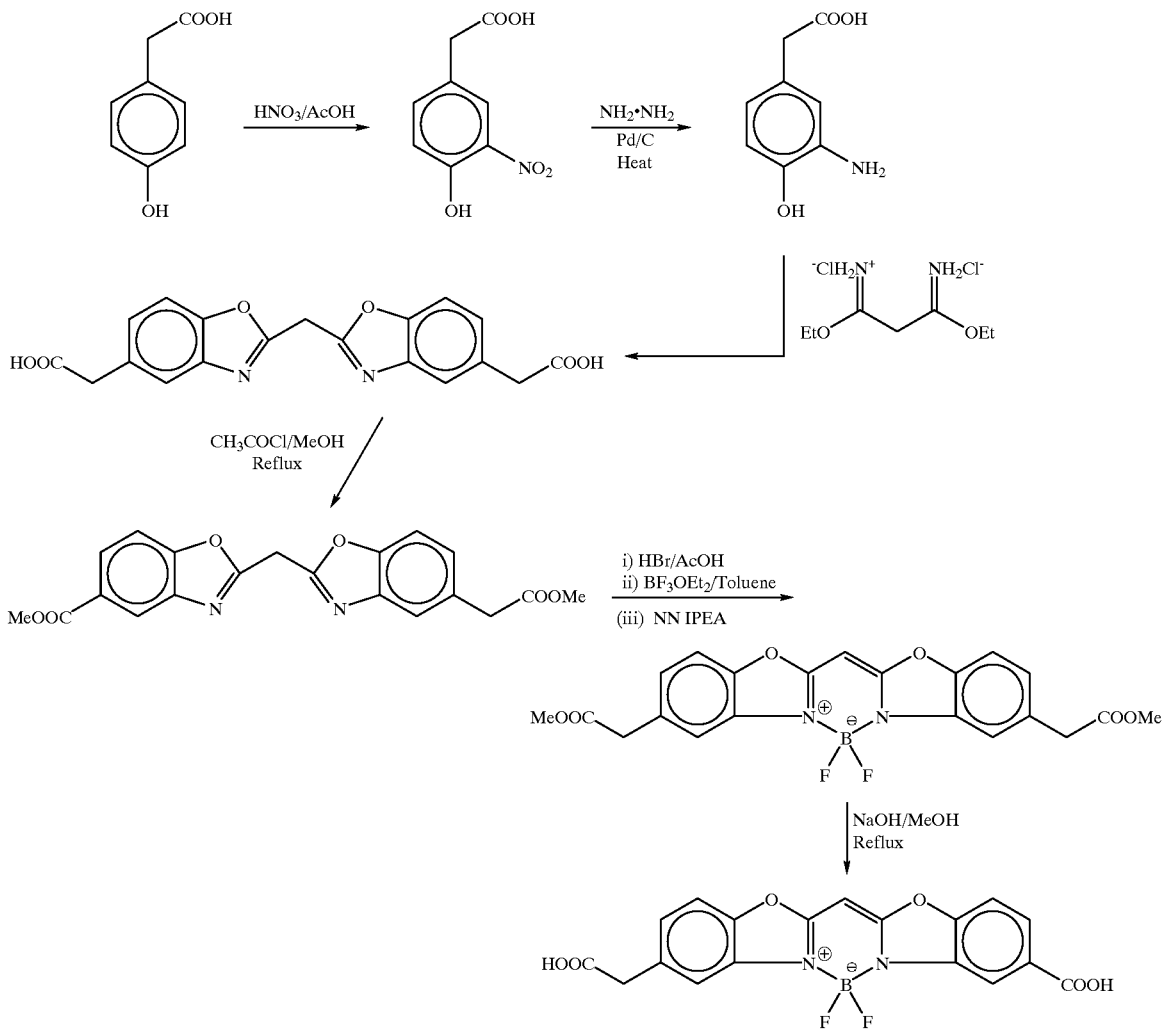

In a first step, carried out according to Humel in Synth. Commun. 15, pages 1081–88 (1985), to a magnetically stirred solution of 100 g (0.65 mole) of 4-hydroxyphenyl acetic acid in 250 ml of glacial acetic acid was added dropwise a mixture of 40 ml of nitric acid (1.4 specific gravity) and 60 ml glacial acetic acid. The glacial acetic acid was warmed to about 45° C. to completely dissolve the 4-hydroxyphenyl acetic acid. Following addition of the nitric acid/acetic acid mixture, stirring of the resulting mixture was continued for one hour at 25° C. and then the flask was chilled in ice water for one hour. The resulting crystals were washed with cold water and air-dried at room temperature, the reaction providing 65% of the theoretical yield of 3-nitro 4-hydroxyphenyl acetic acid.

In a second step, 19.7 g (90.1 mole) of the 3-nitro, 4-hydroxyphenyl acetic acid was dissolved in 160 ml of aqueous 0.625M sodium hydroxide solution. Palladium on charcoal (175 mg palladium, 10% by weight of the catalyst) was added as a catalyst to the resulting solution and then hydrazine hydrate was carefully added dropwise using a syringe over 0.5 hours. The temperature of the mixture was observed to increase to 60° C. due to the reaction. The reaction mixture was further heated to 80° C. and held constant at that temperature for 0.5 hour, and then maintained at that temperature and refluxed for one hour. During refluxing, the orange color of the solution was observed to gradually disappear. After reflux, the reaction vessel was cooled to 25° C. and the mixture was filtered over celite to remove the catalyst. The solvent was then removed from the filtrate to yield 25–30 ml of a concentrate, the pH of which was adjusted to 4–5 with glacial acetic acid. On chilling the acidified concentrate, crystals of 3-amino 4-hydroxyphenyl acetic acid began to separate out. A second crop of crystals was recovered on chilling the acidified concentrate overnight in a refrigerator. 92% of the theoretical yield of 3-amino 3-hydroxyphenyl acetic acid was recovered. Steps 1 and 2 provide an ortho aminophenol derivative having a carboxymethyl group.

In step 3, a modification of the method of McElvain et al., (JACS, 71, 40, 1949), ethyl bisimidate hydrochloride was prepared. 0.66 g (10 mmol) malononitrile was dissolved in 5 ml of dry dioxane. To this solution was added 0.92 g (20 mmol) ethanol. Into this malononitrile solution was injected in one portion 5 ml of a 4M solution of hydrochloric acid in dioxane and the resulting mixture was stirred for 36 hours at room temperature. The resulting thick white slurry was filtered, washed with at least three 50 ml portions of dry ether, and dried under vacuum at room temperature for 1–2 hours. 93% of the theoretical yield of ethyl bisimidate hydrochloride was obtained.

In the fourth step, the ethyl bisimidate hydrochloride was used to link together two molecules of the 3-amino 3-hydroxyphenyl acetic acid prepared in step 2. 1.67 g (10 mmol) of 3-amino 3-hydroxyphenyl acetic acid was suspended in 30 ml of dry methanol in a round bottom flask. 1.15 g (5 mmol) of the freshly prepared ethyl bisimidate hydrochloride was quickly added to the suspension and the temperature of the resulting mixture was raised to reflux when a second portion of 30 ml of dry methanol was added. It was observed that within minutes the solution became clear. As refluxing progressed, the product, bis carboxymethyl benzoxazolyl methane, came out of solution and increased the turbidity of the mixture. Refluxing was maintained for 4 hours, after which the flask was cooled to room temperature and was then cooled in a refrigerator for 12 hours. Bis carboxymethyl benzoxazolyl methane (75% of theoretical yield), in the form of a fine white powder, was recovered following filtration, washing with methanol, and drying.

In Step 5, the product (1.65 g, 4 mmol) from the preceding step was suspended in 25 ml of methanol. 1 ml of acetyl chloride was added in one portion and the suspension immediately became clear. The reaction mixture was heated and maintained at reflux for 3 hours, a white solid forming after 0.5 hour. The reaction vessel was cooled to 25° C. and then the methanol was removed under vacuum. 25 ml of ethyl acetate was then added to the wet white solid, followed by 20 ml of 0.5M aqueous sodium hydroxide. However, a lower molarity sodium hydroxide solution is preferred. After effective contact between the aqueous and organic layers of the mixture, the organic layer was collected, dried over magnesium sulfate and concentrated under a vacuum to provide a viscous colorless oil which included the dimethyl ester of bis carboxymethyl benzoxazolyl methane. Crystallization of the solid ester was not attempted and the oil was used in the next step, but it is believed that the yield for the ester was quantitative.

In the sixth and seventh steps, the hydrobromide quaternary salt of the dimethyl ester of the bis carboxymethyl benzoxazolyl methane is prepared first and the condensation of the salt with boron trifluoride occurs next. These steps are procedurally identical to those for preparation of the compound of Example A.

In a final eighth step, 150 mg of the product of the seventh step, bis carboxymethyl dimethyl ester was suspended in a mixture of 35 ml of methanol and 5 ml of sodium hydroxide (80 mg/ml). The suspension was heated and refluxed for 0.75 hour and, after cooling, the solvent was partially removed under vacuum to yield 3 ml of a concentrate. The pH of the concentrate was adjusted to 4–5 with glacial acetic acid to precipitate out the product. Bis carboxymethyl benzoxazolyl methene boron complex (88% of theoretical yield) in the form of a white powder was recovered from the concentrate after filtration, washing with cold water, and drying in a vacuum at 25° C.

The maximum observed absorptive wavelength for the compound was 362 nm and the maximum emissive wavelength was 386 nm, both measured in methanol. The compound was highly fluorescent.

Example D

Chromophore 12

The synthetic pathway for producing this compound is schematically represented below.

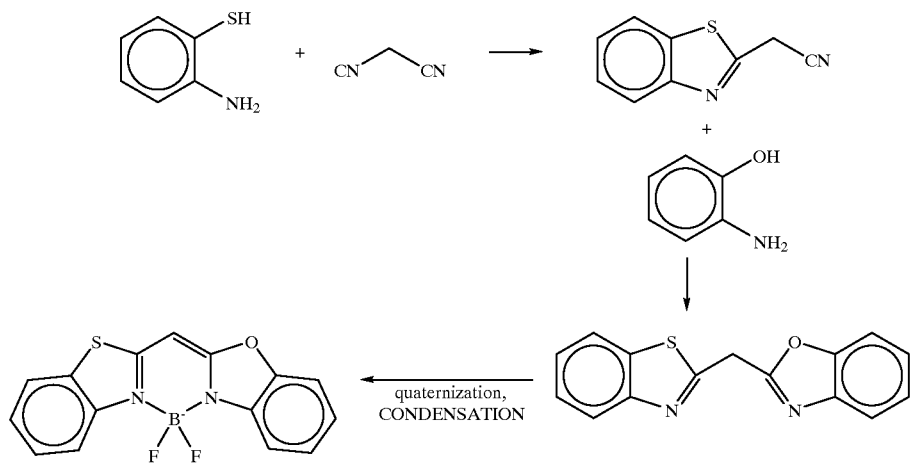

In a first step, 2-cyanomethyl benzothiazole was prepared according to the method of Saito et al. (Synthesis, (3), pp. 210–11 (1983)). 2-amino benzenethiol (10 mmol) and malononitrile (10 mmol) were dissolved in 10 ml of ethanol with a small amount of glacial acetic acid (10 mmol) added. After stirring overnight, a yellow crystalline mass was recovered after filtration and drying, providing 80% of the theoretical yield of 2-cyanomethyl benzothiazole.

In a second step, a 1:1 molar ratio of 2-cyanomethyl benzothiazole and 2-aminophenol were uniformly mixed, ground and transferred to a round bottom flask. Polyphosphoric acid (approx. 80%, 20 ml for 10 mmol scale reaction) was warmed until fluid and then poured into the flask. The flask was then placed in a 185° C. oil bath and heated in a nitrogen environment. After one hour, the flask was removed from the nitrogen environment and the contents were poured over crushed ice and stirred for one hour. The lumps which formed were broken down to yield a brown suspension which was filtered, and the resulting solids were washed with cold water until the washings were neutral. The solids, consisting of 2-(2'-benzoxazolyl) methyl benzothiazole, were then air dried. No yield was recorded.

The final boron-rigidized complex was synthesized from the 2-(2'-benzoxazolyl methyl) benzothiazole by first producing the hydrobromide quaternary salt and then by condensing this salt with boron trifluoride as in the previous Examples A and C. The maximum absorptive wavelength for the compound was 388 nm and the maximum emissive wavelength was 414 nm, both measured in methanol. The chromophore was highly fluorescent in methanol.

Example E

Chromophore 13

The method of preparing this dye is identical to that for preparing bis-benzothiazolylmethene borondifluoride. The introduction of the acetyl group onto the meso-carbon is similar to that of introducing the carboxymethyl group during preparation of reactive bis-benzothiazolylmethene borondifluoride. Instead of using methyl bromoacetate, acetyl chloride was used for the reaction with the sodium salt of bis-benzenthiazolyl methane, The maximum absorptive wavelength for the chromophore 13 was 416 nm measured in methanol. The maximum emissive wavelength was not measured. The chromophore was less fluorescent than the base benzothiazole chromophore. The synthetic procedure to introduce an acetyl group on the bridging carbon atom is as follows:

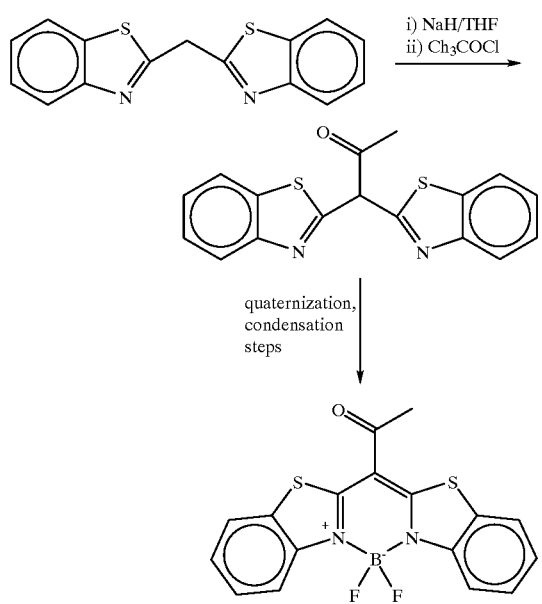

Example F

Benzothiazolyl Pyridylmonomethine Borondifluoride

In a first step, 2-pyridylmethyl benzothiazole was prepared by refluxing a 1:1 molar ratio of 2-cyanomethyl pyridine and 2-amino benzenethiol in ethanol for 8 hours. About 25 ml of ethanol was used for a 10 mmol scale reaction. After the solvent was removed under vacuum, a yellow oil remained. the oil was dissolved in ether and washed with a 0.5M aqueous potassium hydroxide solution to remove unreacted thiol. The organic layer was then washed with a saturated sodium chloride solution, dried over magnesium sulphate and evaporated to again yield a yellow oil reaction product.

The subsequent steps are the quaternization and boron trifluoride condensation steps used in the synthesis process of Example A. The yield for of benzothiazolyl pyridylmonomethine borondifluoride was a moderate 40–50% of theoretical. The maximum absorptive wavelength for the chromophore was 430 nm and the maximum emissive wavelength was 476 nm, both measured in methanol. The chromophore exhibited high fluorescence in methanol.

The reaction pathway is schematically as follows.

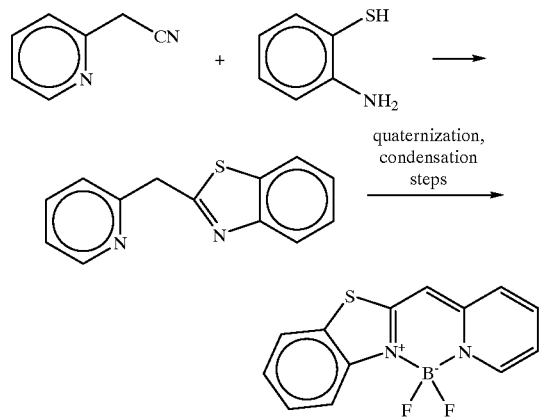

Example G

Chromophore 15

In a first step, bis(2-pyridyl) acetonitrile was prepared by appropriately modifying the method of Newkome et al. (J. Org. Chem., 53, p. 786 (1988)). 980 mg (41 mmol) sodium hydride was suspended in 50 ml of tetrahydrofuran under a nitrogen atmosphere. To the stirred suspension, 1.21 g (10.3 mmol) 2-cyanomethyl pyridine and 1.02 g (10.3 mmol) 2-pyridine was added and the resulting mixture was heated and refluxed for six hours, cooled to 25° C., and the solvent was then removed under vacuum. After quenching the resulting brown mass with water, the mixture was acidified with 0.1N hydrochloric acid and twice extracted with 100 ml portions of chloroform. The organic layer was washed with aqueous saturated sodium chloride solution, dried over magnesium chloride, and concentrated in vacuum. The resulting brown mass was refrigerated overnight to yield crystals of bis(2-pyridyl) acetonitrile after filtration at 50% of the theoretical yield.

The synthesis of the final boron complex then proceeded as with Example A. However, because the bis(2-pyridyl) acetonitrile intermediate was present in the enamine form, no need existed for quaternization prior to the condensation step with boron trifluoride. Although an overall yield for the preparation of this compound was not determined, it is believed that the yield would be comparable to that for the synthesis of Example A. The maximum absorptive wavelength for chromophore 15 was 432 nm and the maximum emissive wavelength was 460 nm, both measured in methanol. The chromophore was very fluorescent in methanol.

The schematic reaction pathway is as follows.

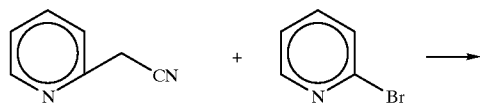

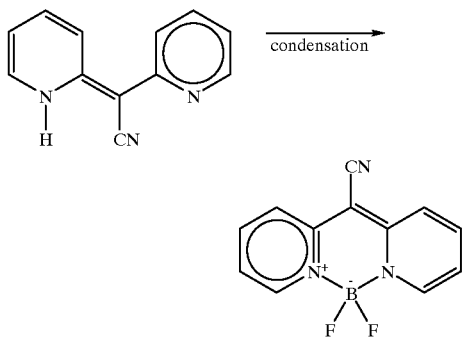

Example H

Bis-Quinolinemethene Borondifluoride 2,2'-bisquinoline methane was prepared in a test tube from quinaldine and 2-chloro quinoline according to the method of U.S. Pat. No. 2,541,400. The crude product produced was used directly in the quaternization and boron trifluoride condensation steps of the synthesis method of Example A. The bis-quinolinemethene borondifluoride produced had a maximum absorptive wavelength of 512 nm and a maximum emissive wavelength of 518 nm, both measured in methanol. The chromophore in methanol exhibited an intense green fluorescence.

The general reaction pathway is as follows.

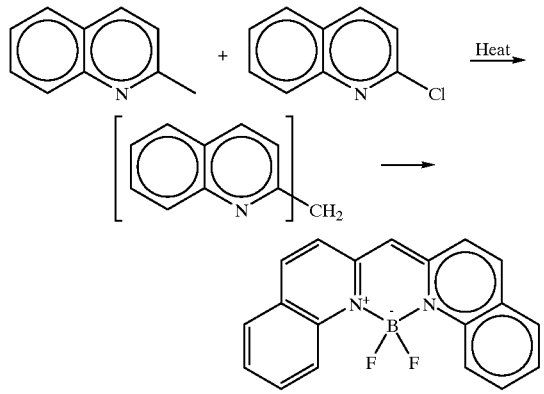

Example I

2(2'-Benzothiazolylmethene)-Quinoline Borondifluoride

2(2'-benzothiazolylmethyl)-quinoline was prepared from 2-methyl benzothiazole and 2-chloro quinoline according to the procedure of U.S. Pat. No. 2,541,400. The resulting crude 2(2'-benzothiazolylmethyl)-quinoline underwent the quaternization and boron difluoride condensation steps of Example A. The resulting 2(2'-benzothiazolylmethene)-quinoline borondifluoride exhibited a maximum absorptive wavelength of 480 nm and a maximum emissive wavelength of 492 nm, both measured in methanol. The chromophore exhibited a green fluorescence.

The general reaction pathway is as follows.

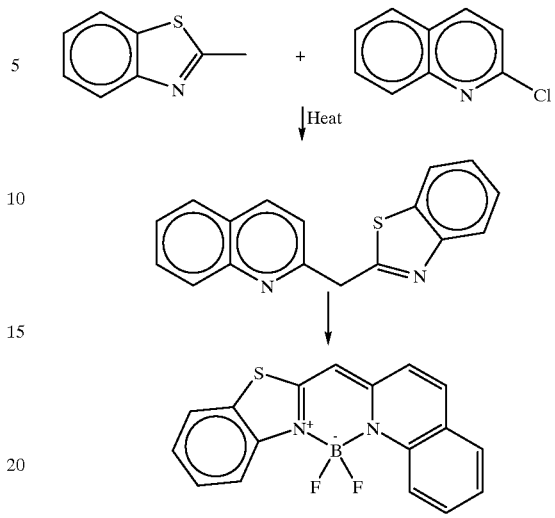

Example J

Protest Labeling

Approximately 20 mg of bis-carboxymethyl benzoxazolyl-methene borondifluoride complex (bis-carboxymethyl dye of Example C) and approximately 25 mg of disuccinimidyl carbonate (DSC) were suspended in 250 microliters of anhydrous dimethyl formamide (DMF). The suspension was heated to 55° C. to dissolve the bis-carboxymethyl dye and the DSC and the solution was maintained at that temperature for one hour. The bis-carboxymethyl dye and DSC reacted to form a disuccinimidyl benzoxazolylmethene borondifluoride complex (Blue 1-OSu), a disuccinimidyl ester of Blue 1. A Sephadex column was prepared with phosphate buffer solution (PBS). To 1 mg sheep IgG protein in 400 microliters $C_3^-/HCO_3^-$ buffer solution (pH 9.6) was added 10–15 microliters of the DMF reaction mixture containing the Blue 1-OSu. The protein/dye solution was vortexed for ten minutes and the solution was then loaded onto the Sephadex column and eluted with PBS. The first fraction that came off of was protein/dye conjugate and fluoresced in the blue region under a 365 nm UV lamp. A portion of the remaining protein/dye complex in the reaction mixture was precipitated out by adding ether and straining, filtering and drying the precipitate.

An experiment was then carried out to label the sheep IgG protein at a higher dye-to-protein, ratio (dye molecules per protein molecule). 1–2 mg of the dried bis carboxymethyl-OSu powder was added directly to 1 mg of protein suspended in 400 microliters of pH 9.6 buffer solution. The resulting bis carboxymethyl-OSu dye IgG protein conjugate was then purified on a Sephadex column. It was estimated that the dye-to-protein ratio of the dye/protein conjugate was 2.7:1. The protein/dye conjugate in PBS was also tested for its emission spectrum and was determined to have a 380 nm excitation maximum wavelength and an emission maximum wavelength range of 425 nm (corrected). The quantum yield of the protein/dye conjugate was calculated to be 0.5.

Example K

Protein Labeling With Sulfonated Dye

In the above experiment using DMF as solvent for the reaction mixture during preparation of the disuccinimidyl derivative, the UV spectrum of the solution on a thin glass slide indicated the presence of dimer. To investigate the use of different solvents, the inventors conducted an experiment wherein a sulfonated boron-rigidized monomethine cyanine derivative of the formula

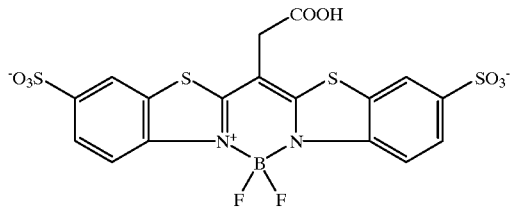

was added to plain HMPA and heated to 100° C. to dissolve the sulfonated compound. The UV spectrum of the solute on a thin glass slide indicated the absence of dimer. Therefore, an additional experiment was carried out using HMPA as the solvent to prepare the disuccinimidyl derivative of a boron-rigidized compound of the present invention. Approximately 5–10 mg of a sulfonated derivative of a thiazole-based compound of the present invention was incubated with approximately 10 mg DSC in 0.25 ml HMPA and 50 microliters pyridine, heated to 100° C. with stirring, and allowed to react for 0.25 hour to provide disuccinimidyl derivative of the thiazole-based compound. The reaction occurred as follows:

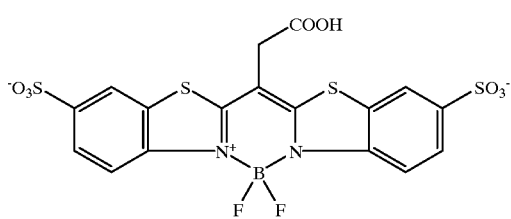
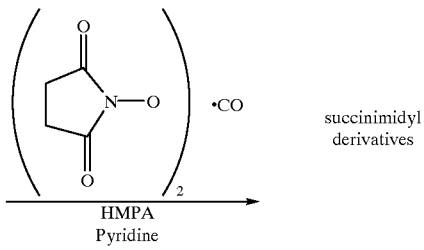

After the 0.25 hour reaction time at temperature, approximately 5–10 microliters of the reaction mixture was removed with a capillary tube and added to a freshly prepared solution of sheep IgG in PBS buffer. After 15 minutes, conjugate of the protein with the disuccinimidyl derivative was separated from unreacted derivative on a Sephadex column. Protein/dye conjugate was separated and, therefore, the disuccinimidyl derivative prepared in HMPA did label protein. It was also determined that the fluorescence of the conjugate did not become quenched and the UV spectrum of the protein/dye conjugate in PBS indicated no dimer formation. Therefore, HMPA appears well-suited as the solvent in the preparation of the disuccinimidyl derivative of the sulfonated boron-bridged complex.

What is claimed:

1. A method for imparting fluorescent properties to a target, the method comprising incubating a target having at least one functional group selected from the group consisting of amino, hydroxyl, phosphoryl, carbonyl, and sulfhydryl groups, and an amount of a fluorescent molecule having the structure

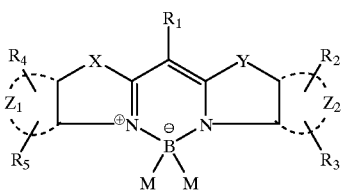

wherein

X and Y are selected from the group consisting of —C(CH$_3$)$_2$—, oxygen, sulfur, —CH=CH—, and >N—W—K where N is nitrogen;

dotted lines Z$_1$ and Z$_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur;

R$_1$, R$_2$, R$_3$, R$_4$ and R$_5$ are selected from the group consisting of —K and —W—K;

M is selected from the group consisting of F and Cl;

W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and K is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramidite, alkylimidate, a arylimidate, acid halide, substituted hydrazines, substituted hydroxylamines, carbodiimides; and
electron donating and withdrawing groups that shift the absorption and emission wavelengths of the fluorescent molecule;

for a period of time sufficient to permit the fluorescent molecule to covalently bind to the at least one functional group of the target.

2. A method for imparting fluorescent properties to a target, the method comprising incubating an amount of a fluorescent molecule having the structure

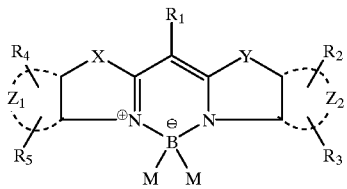

wherein:
X and Y are selected from the group consisting of —C(CH$_3$)$_2$—, oxygen, sulfur, —CH=CH—, and >N—W—K where N is nitrogen;
dotted lines Z$_1$ and Z$_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur;
R$_1$, R$_2$, R$_3$, R$_4$ and R$_5$ are selected from the group consisting of —K and —W—K, and at least one of R$_1$, R$_2$, R$_3$, R$_4$ and R$_5$ is a functional group selected from the group consisting of amino, hydroxyl, phosphoryl, carbonyl, and sulfhydryl;
M is selected from the group consisting of F and Cl;
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
K is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramidite, alkylimidate, arylimidate, acid halide, substituted hydrazines, substituted hydroxylamines, carbodiimides; and
electron donating and withdrawing groups that shift the absorption and emission wavelengths of the fluorescent molecule;
and
a target having at least one reactive group that can covalently bind with the at least one functional group, for a period of time sufficient to permit the at least one reactive group of the target to covalently bind to the at least one functional group of the fluorescent molecule.

3. The method recited in any of claims 1 and 2, wherein the target is selected from the group consisting of nucleotides, nucleic acids, cells, microbes, drugs, toxins, particles, plastic surfaces, glass surfaces, polymers, tissues, amino acids, proteins, antibodies, enzymes, hormones, polysaccharides, lipids, and materials including at least one group selected from the group consisting of amino, hydroxyl, aldehyde, phosphoryl, and sulfhydryl.

4. The method recited in any of claims 1 and 2, wherein the target is selected from the group consisting of cellulose-based material, textiles, petroleum-based products, photographic film, glass, polymers, gel filtration media, and chromatography media.

5. A method of labeling a target, the method comprising incubating the target with an amount of a fluorescent molecule under conditions to form a covalent linkage between the target and the fluorescent molecule, the fluorescent molecule having the structure

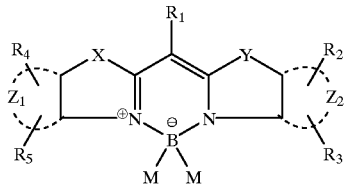

wherein:
X and Y are selected from the group consisting of —C(CH$_3$)$_2$—, oxygen, sulfur, —CH=CH—, and >N—W—K where N is nitrogen;
dotted lines Z$_1$ and Z$_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur;
R$_1$, R$_2$, R$_3$, R$_4$ and R$_5$ are selected from the group consisting of —K and —W—K;
M is selected from the group consisting of F and Cl;
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
K is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramidite, alkylimidate, arylimidate, acid halide, substituted hydrazines, substituted hydroxylamines, carbodiimides; and
electron donating and withdrawing groups that shift the absorption and emission wavelengths of the fluorescent molecule.

6. The method recited in claim 5, wherein the conditions promote formation of the covalent linkage through a reaction selected from a condensation reaction, a reduction reaction, and an oxidation reaction.

7. The method recited in claim 5 wherein the target includes a group selected from the group consisting of amino, hydroxyl, aldehyde, phosphoryl, and sulfhydryl, and further wherein at least one of R$_1$ through R$_5$ of the fluorescent molecule forms a covalent linkage with the reactive group.

8. The method of claim 5 wherein the target is selected from the group consisting of nucleotides, nucleic acids, cells, microbes, drugs, toxins, particles, plastic surfaces, glass surfaces, polymers, tissues, amino acids, proteins, antibodies, enzymes, hormones, polysaccharides, lipids, and materials including at least one group selected from the group consisting of amino, hydroxyl, aldehyde, phosphoryl, and sulfhydryl.

9. A method of imparting fluorescent properties to a charged target, the method comprising incubating the target with an amount of a fluorescent molecule having the structure

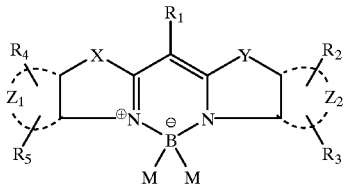

wherein:
X and Y are selected from the group consisting of —C(CH$_3$)$_2$—, oxygen, sulfur, —CH=CH—, and >N—W—K where N is nitrogen;
dotted lines $Z_1$ and $Z_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur;
$R_1$, $R_2$, $R_3$, $R_4$ and $R_5$ are selected from the group consisting of —K and —W—K, and at least one of $R_1$ through $R_5$ is a charged group;
M is selected from the group consisting of F and Cl;
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
K is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramidite, alkylimidate, arylimidate, acid halide, substituted hydrazines, substituted hydroxylamines, carbodiimides; and
electron donating and withdrawing groups that shift the absorption and emission wavelengths of the fluorescent molecule;
under conditions to noncovalently associate the fluorescent molecule with the target.

10. The method of claim 9, wherein at least one of $R_1$ through $R_5$ is a charged group selected from the group consisting of amino and quaternary amino groups.

11. The method recited in claim 9, wherein the target is selected from the group consisting of DNA and RNA.

12. A method for detecting a target in a medium, the method comprising:
(i) incubating a primary component having an affinity for the target with an amount of a fluorescent molecule having the structure

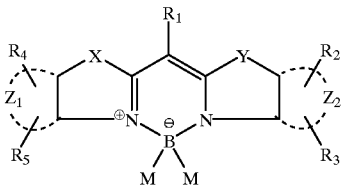

wherein:
X and Y are selected from the group consisting of —C(CH$_3$)$_2$—, oxygen, sulfur, —CH=CH—, and >N—W—K where N is nitrogen;
dotted lines $Z_1$ and $Z_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur;
$R_1$, $R_2$, $R_3$, $R_4$ and $R_5$ are selected from the group consisting of —K and —W—K;
M is selected from the group consisting of F and Cl;
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
K is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanates, isocyanate, iodoacetamide, maleimide, sulfonyl halide, phosphoramidite, alkylimidate, arylimidate, acid halide, substituted hydrazines, substituted hydroxylamines, carbodiimides; and
electron donating and withdrawing groups that shift the absorption and emission wavelengths of the fluorescent molecule;
under conditions to form a covalent linkage between the primary component and the flourescent molecule to thereby provide a fluorescently labeled primary component; and
(ii) incubating an amount of the fluorescently labeled primary component with the medium under conditions to bind at least a portion of the flourescently labeled primary component with the target to thereby provide a fluorescently labeled target.

13. The method recited in claim 12, wherein the target is an antibody and the primary component is an antigen, the antigen having an affinity for the antibody.

14. The method recited in claim 12, wherein the primary component is an antibody and the target is an antigen, the antibody having an affinity for the antigen.

15. The method recited in claim 12, wherein the primary component is an antibody and the target is a cell, the antibody having an affinity for the cell.

16. The method recited in claim 12, wherein the target is at least one protein.

17. The method recited in claim 12, further comprising:
(iii) isolating at least a portion of the fluorescently labeled target from the medium to thereby provide an isolated portion.

18. The method recited in claim 17, further comprising:
(iv) determining the intensity of fluorescence of the isolated portion.

19. A method for quantifying a plurality of targets in a medium, the method comprising:
(i) incubating at least a portion of the medium with an amount of a fluorescent molecule having the structure

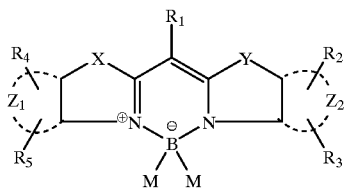

wherein:
X and Y are selected from the group consisting of —C(CH$_3$)$_2$—, oxygen, sulfur, —CH=CH—, and >N—W—K where N is nitrogen;
dotted lines Z$_1$ and Z$_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur;
R$_1$, R$_2$, R$_3$, R$_4$ and R$_5$ are selected from the group consisting of —K and —W—K;
M is selected from the group consisting of F and Cl;
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
K is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramidite, alkylimidate, arylimidate, acid halide, substituted hydrazines, substituted hydroxylamines, carbodiimides; and
electron donating and withdrawing groups that shift the absorption and emission wavelengths of the fluorescent molecule;

under conditions to form a covalent linkage between the fluorescent molecule and the plurality of targets, thereby providing a plurality of fluorescently labeled targets;
(ii) separating the plurality of fluorescently labeled targets into separate portions according to at least one property of the targets; and
(iii) determining the intensity of fluorescence of one or more of the separate portions.

20. The method recited in claim 19, wherein at least one of the targets is a protein.

21. The method recited in claim 19, wherein separating the plurality of fluorescently labeled targets comprises isolating fluorescently labeled targets by chromatography.

22. A method for quantifying a plurality of targets in a medium, the method comprising:
incubating a primary component having an affinity for the targets with an amount of a fluorescent molecule having the structure

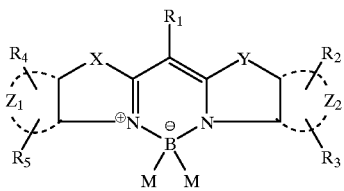

wherein:
X and Y are selected from the group consisting of —C(CH$_3$)$_2$—, oxygen, sulfur, —CH=CH—, and >N—W—K where N is nitrogen;
dotted lines Z$_1$ and Z$_2$ represent the atoms necessary to complete a structure selected from the group consisting of one ring, two fused rings, and three fused rings, each said ring having five or six atoms, and each said ring comprising carbon atoms and, optionally, no more than two atoms selected from oxygen, nitrogen and sulfur;
R$_1$, R$_2$, R$_3$, R$_4$ and R$_5$ are selected from the group consisting of —K and —W—K;
M is selected from the group consisting of F and Cl;
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
K is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramidite, alkylimidate, arylimidate, acid halide, substituted hydrazines, substituted hydroxylamines, carbodiimides; and
electron donating and withdrawing groups that shift the absorption and emission wavelengths of the fluorescent molecule;

under conditions to form a covalent linkage between the primary component and the fluorescent molecule to provide a fluorescently labeled primary component;

(ii) incubating an amount of the fluorescently labeled primary component with at least a portion of the medium under conditions to bind at least a portion of the fluorescently labeled primary component with the plurality of targets to provide fluorescently labeled targets; and (iii) separating the fluorescently labeled targets into separate portions according to at least one property of the targets.

23. The method recited in claim 22, further comprising:
(iv) determining the intensity of fluoresence of the separate portions.

24. The method recited in claim 22, wherein the targets are cells and the primary component is an antibody, the antibody having an affinity for the cells.

25. The method recited in claim 22, wherein the targets are antibodies and the primary component is an antigen, the antibodies having an affinity for the antigen.

26. The method recited in claim 22, wherein the targets are antigens and the primary component is an antibody, the antigens having an affinity for the antibody.

* * * * *

UNITED STATES PATENT AND TRADEMARK OFFICE
CERTIFICATE OF CORRECTION

PATENT NO.    : 6,207,464 B1
DATED         : March 27, 2001
INVENTOR(S)   : Waggoner et al.

It is certified that error appears in the above-identified patent and that said Letters Patent is hereby corrected as shown below:

Column 7,
Line 63, delete "$\geq C(CH_3)_2$" and replace therewith -- $C(CH_3)_2$ --

Column 29,
Line 49, add the word "to" before "a mixture"

Column 36,
Line 26, remove "Protest Labeling" in heading of Example 3 and replace therewith -- Protein Labeling --
Line 39, delete "$C_3$- /HCO" and replace therewith -- $CO_3$-/HCO --

Signed and Sealed this

Twenty-eighth Day of January, 2003

JAMES E. ROGAN
*Director of the United States Patent and Trademark Office*